(12) United States Patent
Leopold et al.

(10) Patent No.: US 8,984,733 B2
(45) Date of Patent: Mar. 24, 2015

(54) BODILY LUMEN OCCLUSION

(71) Applicant: Artventive Medical Group, Inc., San Marcos, CA (US)

(72) Inventors: Andrew Leopold, Hawthorn Woods, IL (US); Leon Rudakov, San Marcos, CA (US); Kelly Jensen, Palatine, IL (US)

(73) Assignee: Artventive Medical Group, Inc., San Marcos, CA (US)

( * ) Notice: Subject to any disclaimer, the term of this patent is extended or adjusted under 35 U.S.C. 154(b) by 0 days.

(21) Appl. No.: 14/044,794

(22) Filed: Oct. 2, 2013

(65) Prior Publication Data

US 2014/0215792 A1 Aug. 7, 2014

Related U.S. Application Data

(63) Continuation-in-part of application No. 13/828,974, filed on Mar. 14, 2013.

(60) Provisional application No. 61/761,195, filed on Feb. 5, 2013.

(51) Int. Cl.
*A61B 17/00* (2006.01)
*A61B 17/12* (2006.01)

(52) U.S. Cl.
CPC ................................ *A61B 17/12109* (2013.01)
USPC .......................................................... 29/428

(58) Field of Classification Search
CPC ............. A61F 2/07; A61F 2/88; A61F 2/885; A61F 2/95; A61F 2/966; A61F 2/954; A61F 2/958; A61F 2002/9665; A16B 17/12031

USPC ................... 623/1.11, 1.12, 1.14, 1.22, 1.23; 606/191

See application file for complete search history.

(56) References Cited

U.S. PATENT DOCUMENTS 3,805,767 A  4/1974 Erb
3,868,956 A  3/1975 Alfidi et al.
(Continued)

FOREIGN PATENT DOCUMENTS

CN  2527227 Y  12/2002
EP  1166721 A2  1/2002
(Continued)

OTHER PUBLICATIONS

International Search Report and Written Opinion dated Apr. 25, 2014, which issued in International Application No. PCT/US2014/014889.
(Continued)

*Primary Examiner* — Alexander P Taousakis
*Assistant Examiner* — Lee A Holly
(74) *Attorney, Agent, or Firm* — James W. Hill; Nathan S. Smith; McDermott Will & Emery, LLP

(57) ABSTRACT

An occlusion system can include an expandable implant that can be delivered to a bodily lumen. The implant can be carried on an engagement section of a catheter used in the system. The implant can be assembled onto the catheter by coupling a cover member of the implant with a support member of the implant. When assembled, the system can be advantageously configured to have a low delivery profile to facilitate delivery through catheters having a size of less than 7 Fr, and in some cases, less than 6 Fr.

13 Claims, 20 Drawing Sheets

(56) References Cited

U.S. PATENT DOCUMENTS

| | | | |
|---|---|---|---|
| 3,918,431 A | 11/1975 | Sinnreich |
| 4,013,063 A | 3/1977 | Bucalo |
| 4,245,623 A | 1/1981 | Erb |
| 4,553,545 A | 11/1985 | Maass et al. |
| 4,649,922 A | 3/1987 | Wiktor |
| 4,682,592 A | 7/1987 | Thorsgard |
| 4,705,517 A | 11/1987 | DiPisa, Jr. |
| 4,706,671 A | 11/1987 | Weinrib |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,800,882 A | 1/1989 | Gianturco |
| 4,827,946 A | 5/1989 | Kaali et al. |
| 4,913,141 A | 4/1990 | Hillstead |
| 4,969,890 A | 11/1990 | Sugita et al. |
| 5,037,427 A | 8/1991 | Harada et al. |
| 5,065,751 A | 11/1991 | Wolf |
| 5,089,005 A | 2/1992 | Harada |
| 5,102,417 A | 4/1992 | Palmaz |
| 5,147,370 A | 9/1992 | McNamara et al. |
| 5,234,437 A | 8/1993 | Sepetka |
| 5,242,451 A | 9/1993 | Harada et al. |
| 5,304,198 A | 4/1994 | Samson |
| 5,324,306 A | 6/1994 | Makower et al. |
| 5,334,210 A | 8/1994 | Gianturco |
| 5,342,387 A | 8/1994 | Summers |
| 5,372,600 A | 12/1994 | Beyar et al. |
| 5,417,708 A | 5/1995 | Hall et al. |
| 5,474,089 A | 12/1995 | Waynant |
| 5,476,505 A * | 12/1995 | Limon ..................... 623/1.11 |
| 5,499,995 A | 3/1996 | Teirstein |
| 5,536,274 A | 7/1996 | Neuss |
| 5,562,641 A | 10/1996 | Flomenblit et al. |
| 5,562,698 A | 10/1996 | Parker |
| 5,607,445 A | 3/1997 | Summers |
| 5,656,036 A | 8/1997 | Palmaz |
| 5,674,287 A | 10/1997 | Slepian et al. |
| 5,693,083 A | 12/1997 | Baker et al. |
| 5,725,552 A | 3/1998 | Kotula et al. |
| 5,733,329 A | 3/1998 | Wallace et al. |
| 5,772,668 A * | 6/1998 | Summers et al. ............ 623/1.11 |
| 5,782,860 A | 7/1998 | Epstein et al. |
| 5,797,952 A | 8/1998 | Klein |
| 5,797,953 A | 8/1998 | Tekulve |
| 5,830,222 A | 11/1998 | Makower |
| 5,842,621 A | 12/1998 | Gschwind |
| 5,902,266 A | 5/1999 | Leone et al. |
| 5,922,009 A | 7/1999 | Epstein et al. |
| 5,925,063 A | 7/1999 | Khosravi |
| 5,925,074 A | 7/1999 | Gingras et al. |
| 5,928,260 A | 7/1999 | Chin et al. |
| 5,944,738 A | 8/1999 | Amplatz et al. |
| 5,954,766 A | 9/1999 | Zadno-Azizi et al. |
| 5,979,446 A | 11/1999 | Loy |
| 6,010,517 A | 1/2000 | Baccaro |
| 6,019,779 A | 2/2000 | Thorud et al. |
| 6,024,765 A | 2/2000 | Wallace et al. |
| 6,056,770 A | 5/2000 | Epstein et al. |
| 6,059,825 A | 5/2000 | Hobbs et al. |
| 6,117,157 A | 9/2000 | Tekulve |
| 6,123,715 A | 9/2000 | Amplatz |
| 6,168,622 B1 | 1/2001 | Mazzocchi |
| 6,190,353 B1 | 2/2001 | Makower et al. |
| 6,210,338 B1 | 4/2001 | Afremov et al. |
| 6,214,042 B1 | 4/2001 | Jacobsen et al. |
| 6,241,678 B1 | 6/2001 | Afremov et al. |
| 6,241,758 B1 | 6/2001 | Cox |
| 6,245,090 B1 | 6/2001 | Gilson et al. |
| 6,248,122 B1 | 6/2001 | Klumb et al. |
| 6,283,983 B1 | 9/2001 | Makower et al. |
| 6,334,864 B1 | 1/2002 | Amplatz et al. |
| 6,346,118 B1 | 2/2002 | Baker et al. |
| 6,361,558 B1 | 3/2002 | Hieshima et al. |
| 6,368,339 B1 | 4/2002 | Amplatz |
| 6,371,953 B1 | 4/2002 | Beyar et al. |
| 6,371,979 B1 | 4/2002 | Beyar et al. |
| 6,402,760 B1 | 6/2002 | Fedida |
| 6,402,772 B1 | 6/2002 | Amplatz et al. |
| 6,432,116 B1 | 8/2002 | Callister et al. |
| 6,432,127 B1 | 8/2002 | Kim et al. |
| 6,447,531 B1 | 9/2002 | Amplatz |
| 6,451,025 B1 | 9/2002 | Jervis |
| 6,454,780 B1 | 9/2002 | Wallace |
| 6,464,712 B1 | 10/2002 | Epstein et al. |
| 6,468,301 B1 | 10/2002 | Amplatz et al. |
| 6,506,204 B2 | 1/2003 | Mazzocchi |
| 6,533,805 B1 | 3/2003 | Jervis |
| 6,550,480 B2 | 4/2003 | Feldman et al. |
| 6,554,849 B1 | 4/2003 | Jones et al. |
| 6,562,064 B1 | 5/2003 | deBeer |
| 6,572,643 B1 | 6/2003 | Gharibadeh |
| 6,579,303 B2 | 6/2003 | Amplatz |
| 6,585,760 B1 | 7/2003 | Fogarty |
| 6,599,308 B2 | 7/2003 | Amplatz |
| 6,602,271 B2 | 8/2003 | Adams et al. |
| 6,616,675 B1 | 9/2003 | Evard et al. |
| 6,623,518 B2 | 9/2003 | Thompson et al. |
| 6,629,981 B2 | 10/2003 | Bui et al. |
| 6,638,243 B2 | 10/2003 | Kupiecki |
| 6,638,257 B2 | 10/2003 | Amplatz |
| 6,638,293 B1 | 10/2003 | Makower et al. |
| 6,645,237 B2 | 11/2003 | Klumb et al. |
| 6,656,207 B2 | 12/2003 | Taylor et al. |
| 6,660,020 B2 | 12/2003 | Wallace et al. |
| 6,660,032 B2 | 12/2003 | Klumb et al. |
| 6,663,666 B1 | 12/2003 | Quiachon et al. |
| 6,682,546 B2 | 1/2004 | Amplatz |
| 6,689,148 B2 | 2/2004 | Sawhney et al. |
| 6,702,846 B2 | 3/2004 | Mikus et al. |
| 6,719,781 B1 | 4/2004 | Kim |
| 6,790,218 B2 | 9/2004 | Jayaraman |
| 6,849,081 B2 | 2/2005 | Sepetka et al. |
| 6,872,211 B2 | 3/2005 | White et al. |
| 6,890,341 B2 | 5/2005 | Dieck et al. |
| 6,899,730 B1 | 5/2005 | Rivelli, Jr. |
| 6,936,058 B2 | 8/2005 | Forde et al. |
| 6,974,473 B2 | 12/2005 | Barclay et al. |
| 6,984,244 B2 | 1/2006 | Perez et al. |
| 7,001,409 B2 | 2/2006 | Amplatz |
| 7,011,671 B2 | 3/2006 | Welch |
| 7,144,408 B2 | 12/2006 | Keegan et al. |
| 7,152,605 B2 | 12/2006 | Khairkhahan et al. |
| 7,220,270 B2 | 5/2007 | Sawhney et al. |
| 7,270,668 B2 | 9/2007 | Andreas et al. |
| 7,276,077 B2 | 10/2007 | Zadno-Azizi et al. |
| 7,294,146 B2 | 11/2007 | Chew et al. |
| 7,303,571 B2 | 12/2007 | Makower et al. |
| 7,387,641 B2 | 6/2008 | Schmitt |
| 7,396,362 B2 | 7/2008 | Jervis |
| 7,398,780 B2 | 7/2008 | Callister et al. |
| 7,458,986 B2 | 12/2008 | Schmitt |
| 7,476,232 B2 | 1/2009 | Deal |
| 7,582,100 B2 | 9/2009 | Johnson et al. |
| 7,597,704 B2 | 10/2009 | Frazier et al. |
| 7,604,649 B2 | 10/2009 | McGuckin, Jr. et al. |
| 7,632,291 B2 | 12/2009 | Stephens et al. |
| 7,647,930 B2 | 1/2010 | Ginn |
| 7,651,521 B2 | 1/2010 | Ton et al. |
| 7,666,204 B2 | 2/2010 | Thornton et al. |
| 7,682,673 B2 | 3/2010 | Houston et al. |
| 7,691,124 B2 | 4/2010 | Balgobin |
| 7,699,056 B2 | 4/2010 | Tran et al. |
| 7,740,616 B2 | 6/2010 | Smith et al. |
| 7,771,463 B2 | 8/2010 | Ton et al. |
| 7,785,343 B2 | 8/2010 | Johnson et al. |
| 7,785,631 B2 | 8/2010 | Roser et al. |
| 7,789,860 B2 | 9/2010 | Brady et al. |
| 7,789,892 B2 | 9/2010 | Johnson et al. |
| 7,803,177 B2 | 9/2010 | Hartley et al. |
| 7,854,747 B2 | 12/2010 | Johnson et al. |
| 7,955,343 B2 | 6/2011 | Makower et al. |
| 7,967,837 B2 | 6/2011 | Vale |
| 7,985,250 B2 | 7/2011 | Kaufmann et al. |

(56) References Cited

U.S. PATENT DOCUMENTS

| | | |
|---|---|---|
| 7,992,565 B2 | 8/2011 | McGuckin, Jr. et al. |
| 8,016,870 B2 | 9/2011 | Chew et al. |
| 8,016,880 B2 | 9/2011 | Cook et al. |
| 8,043,357 B2 | 10/2011 | Hartley |
| 8,100,958 B2 | 1/2012 | Fischer et al. |
| 8,110,267 B2 | 2/2012 | Houston et al. |
| 8,114,114 B2 | 2/2012 | Belson |
| 8,142,456 B2 | 3/2012 | Rosqueta et al. |
| 8,162,970 B2 | 4/2012 | Gilson et al. |
| 8,226,679 B2 | 7/2012 | Johnson et al. |
| 8,226,704 B2 | 7/2012 | Caro et al. |
| 8,308,754 B2 | 11/2012 | Belson |
| 8,323,305 B2 | 12/2012 | Epstein et al. |
| 8,323,350 B2 | 12/2012 | Nissl |
| 8,328,840 B2 | 12/2012 | Gailloud et al. |
| 8,333,783 B2 | 12/2012 | Braun et al. |
| 8,333,796 B2 | 12/2012 | Tompkins et al. |
| 8,343,167 B2 | 1/2013 | Henson |
| 8,348,994 B2 | 1/2013 | Leopold et al. |
| 8,382,771 B2 | 2/2013 | Gellman et al. |
| 8,382,821 B2 | 2/2013 | Richter |
| 8,398,700 B2 | 3/2013 | Leopold et al. |
| 8,425,549 B2 | 4/2013 | Lenker et al. |
| 8,430,904 B2 | 4/2013 | Belson |
| 8,663,301 B2 | 3/2014 | Riina et al. |
| 2001/0007946 A1 | 7/2001 | Lenker et al. |
| 2001/0031981 A1 | 10/2001 | Evans et al. |
| 2001/0044648 A1 | 11/2001 | Wolinsky et al. |
| 2001/0046518 A1 | 11/2001 | Sawhney |
| 2002/0007206 A1 | 1/2002 | Bui et al. |
| 2002/0091439 A1 | 7/2002 | Baker et al. |
| 2002/0099437 A1 | 7/2002 | Anson et al. |
| 2002/0107565 A1 | 8/2002 | Greenhalgh |
| 2002/0143362 A1 | 10/2002 | Macoviak et al. |
| 2002/0198588 A1 | 12/2002 | Armstrong et al. |
| 2003/0114922 A1 | 6/2003 | Iwasaka et al. |
| 2003/0125798 A1 | 7/2003 | Martin |
| 2003/0153972 A1 | 8/2003 | Helmus |
| 2003/0163146 A1 | 8/2003 | Epstein et al. |
| 2003/0171801 A1 | 9/2003 | Bates |
| 2003/0187474 A1 | 10/2003 | Keegan et al. |
| 2003/0187495 A1 | 10/2003 | Cully et al. |
| 2003/0216679 A1 | 11/2003 | Wolf et al. |
| 2003/0229366 A1 | 12/2003 | Reggie et al. |
| 2004/0010282 A1 | 1/2004 | Kusleika |
| 2004/0029994 A1 | 2/2004 | Cheng et al. |
| 2004/0055606 A1 | 3/2004 | Hendricksen et al. |
| 2004/0073252 A1 | 4/2004 | Goldberg et al. |
| 2004/0147869 A1 | 7/2004 | Wolf et al. |
| 2004/0153118 A1 | 8/2004 | Clubb et al. |
| 2004/0158308 A1 | 8/2004 | Hogendijk et al. |
| 2004/0193141 A1 | 9/2004 | Leopold et al. |
| 2004/0220663 A1 | 11/2004 | Rivelli |
| 2004/0225286 A1 | 11/2004 | Elliott |
| 2004/0243219 A1 | 12/2004 | Fischer et al. |
| 2004/0249342 A1 | 12/2004 | Khosravi et al. |
| 2004/0254517 A1 | 12/2004 | Quiroz-Mercado et al. |
| 2004/0260384 A1 | 12/2004 | Allen |
| 2005/0027305 A1 | 2/2005 | Shiu et al. |
| 2005/0033409 A1 | 2/2005 | Burke et al. |
| 2005/0043759 A1 | 2/2005 | Chanduszko |
| 2005/0055079 A1 | 3/2005 | Duran |
| 2005/0055082 A1 | 3/2005 | Ben Muvhar et al. |
| 2005/0113902 A1 | 5/2005 | Geiser et al. |
| 2005/0137681 A1 | 6/2005 | Shoemaker et al. |
| 2005/0165442 A1 | 7/2005 | Thinnes et al. |
| 2005/0192616 A1 | 9/2005 | Callister et al. |
| 2005/0209675 A1 | 9/2005 | Ton et al. |
| 2005/0288684 A1 | 12/2005 | Aronson et al. |
| 2006/0009798 A1 | 1/2006 | Callister et al. |
| 2006/0052822 A1 | 3/2006 | Mirizzi et al. |
| 2006/0119714 A1 | 6/2006 | Tamura et al. |
| 2006/0149359 A1 | 7/2006 | Richter et al. |
| 2006/0162731 A1 | 7/2006 | Wondka et al. |
| 2006/0178727 A1 | 8/2006 | Richter |
| 2006/0184089 A1 | 8/2006 | Makower et al. |
| 2006/0200191 A1 | 9/2006 | Zadno-Azizi |
| 2006/0241675 A1 | 10/2006 | Johnson et al. |
| 2006/0241690 A1 | 10/2006 | Amplatz et al. |
| 2007/0038178 A1 | 2/2007 | Kusleika |
| 2007/0043419 A1 | 2/2007 | Nikolchev et al. |
| 2007/0060946 A1 | 3/2007 | Keegan et al. |
| 2007/0088388 A1 | 4/2007 | Opolski et al. |
| 2007/0112381 A1 | 5/2007 | Figulla et al. |
| 2007/0118209 A1 | 5/2007 | Strecker |
| 2007/0129753 A1 | 6/2007 | Quinn et al. |
| 2007/0135826 A1 | 6/2007 | Zaver et al. |
| 2007/0150045 A1 | 6/2007 | Ferrera |
| 2007/0156224 A1 | 7/2007 | Cioanta et al. |
| 2007/0163601 A1 | 7/2007 | Pollock et al. |
| 2007/0168018 A1 | 7/2007 | Amplatz et al. |
| 2007/0168019 A1 | 7/2007 | Amplatz et al. |
| 2007/0203503 A1 | 8/2007 | Salahieh et al. |
| 2007/0221230 A1 | 9/2007 | Thompson et al. |
| 2007/0239191 A1 | 10/2007 | Ramzipoor |
| 2007/0247680 A1 | 10/2007 | Nakane et al. |
| 2007/0265656 A1 | 11/2007 | Amplatz et al. |
| 2007/0265658 A1 | 11/2007 | Nelson et al. |
| 2008/0017201 A1 | 1/2008 | Sawhney |
| 2008/0045996 A1 | 2/2008 | Makower et al. |
| 2008/0086214 A1 | 4/2008 | Hardin et al. |
| 2008/0103522 A1 | 5/2008 | Steingisser et al. |
| 2008/0132906 A1 | 6/2008 | Rasmussen |
| 2008/0178890 A1 | 7/2008 | Townsend et al. |
| 2008/0200945 A1 | 8/2008 | Amplatz et al. |
| 2008/0215087 A1 | 9/2008 | Pavcnik et al. |
| 2008/0221600 A1 | 9/2008 | Dieck et al. |
| 2008/0269719 A1 | 10/2008 | Balgobin et al. |
| 2008/0302368 A1 | 12/2008 | McGuckin, Jr. et al. |
| 2009/0005847 A1 | 1/2009 | Adams |
| 2009/0018562 A1 | 1/2009 | Amplatz et al. |
| 2009/0018636 A1 | 1/2009 | Gailloud et al. |
| 2009/0025820 A1 | 1/2009 | Adams |
| 2009/0030497 A1 | 1/2009 | Metcalf et al. |
| 2009/0043330 A1 | 2/2009 | To |
| 2009/0062841 A1 | 3/2009 | Amplatz et al. |
| 2009/0078270 A1 | 3/2009 | Meier et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0131959 A1 | 5/2009 | Rolland |
| 2009/0138078 A1 | 5/2009 | Paul, Jr. et al. |
| 2009/0157053 A1 | 6/2009 | Davis et al. |
| 2009/0171386 A1 | 7/2009 | Amplatz et al. |
| 2009/0178682 A1 | 7/2009 | Tal et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0216185 A1 | 8/2009 | Gregorich et al. |
| 2009/0240326 A1 | 9/2009 | Wilson et al. |
| 2009/0276029 A1 | 11/2009 | Caro et al. |
| 2009/0276039 A1 | 11/2009 | Meretei |
| 2009/0277455 A1 | 11/2009 | Lee-Sepsick et al. |
| 2009/0281610 A1 | 11/2009 | Parker |
| 2010/0006105 A1 | 1/2010 | Carter et al. |
| 2010/0030321 A1 | 2/2010 | Mach |
| 2010/0049307 A1 | 2/2010 | Ren |
| 2010/0057194 A1 | 3/2010 | Ryan |
| 2010/0063578 A1 | 3/2010 | Ren et al. |
| 2010/0063582 A1 | 3/2010 | Rudakov |
| 2010/0089406 A1 | 4/2010 | Kachiguina |
| 2010/0106235 A1 | 4/2010 | Kariniemi et al. |
| 2010/0114307 A1 | 5/2010 | Agnew et al. |
| 2010/0121370 A1 | 5/2010 | Kariniemi |
| 2010/0174269 A1 | 7/2010 | Tompkins et al. |
| 2010/0198328 A1 | 8/2010 | Hartley et al. |
| 2010/0223046 A1 | 9/2010 | Bucchieri et al. |
| 2010/0223048 A1 | 9/2010 | Lauder |
| 2010/0249691 A1 | 9/2010 | Van Der Mooren et al. |
| 2010/0268260 A1 | 10/2010 | Riina et al. |
| 2010/0294282 A1 | 11/2010 | Chu et al. |
| 2010/0312268 A1 | 12/2010 | Belson |
| 2010/0318178 A1 | 12/2010 | Rapaport et al. |

(56) References Cited

U.S. PATENT DOCUMENTS

| | | |
|---|---|---|
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0029067 A1 | 2/2011 | McGuckin, Jr. et al. |
| 2011/0040371 A1 | 2/2011 | Hanssen et al. |
| 2011/0124958 A1 | 5/2011 | Nelson |
| 2011/0125132 A1 | 5/2011 | Krolik et al. |
| 2011/0202087 A1 | 8/2011 | Vale |
| 2011/0202129 A1 | 8/2011 | Fofsell |
| 2011/0218479 A1 | 9/2011 | Rottenberg et al. |
| 2011/0264132 A1 | 10/2011 | Strauss et al. |
| 2011/0264195 A1 | 10/2011 | Griswold |
| 2011/0282343 A1 | 11/2011 | Kunis |
| 2011/0301630 A1 | 12/2011 | Hendriksen et al. |
| 2011/0313506 A1 | 12/2011 | Ray et al. |
| 2011/0319906 A1 | 12/2011 | Rudakov et al. |
| 2012/0010556 A1 | 1/2012 | Faul et al. |
| 2012/0022572 A1 | 1/2012 | Braun et al. |
| 2012/0083822 A1 | 4/2012 | Anukhin et al. |
| 2012/0089216 A1 | 4/2012 | Rapaport et al. |
| 2012/0095489 A1* | 4/2012 | Rudakov et al. ............... 606/191 |
| 2012/0101510 A1 | 4/2012 | Lenker et al. |
| 2012/0116350 A1 | 5/2012 | Strauss et al. |
| 2012/0123511 A1 | 5/2012 | Brown |
| 2012/0123514 A1 | 5/2012 | Kunis |
| 2012/0143301 A1 | 6/2012 | Maslanka et al. |
| 2012/0172911 A1 | 7/2012 | Welch |
| 2012/0192872 A1 | 8/2012 | Rudakov et al. |
| 2012/0209310 A1 | 8/2012 | Chen et al. |
| 2012/0239077 A1 | 9/2012 | Zaver et al. |
| 2012/0245620 A1 | 9/2012 | Gilson et al. |
| 2012/0245668 A1 | 9/2012 | Kariniemi et al. |
| 2012/0259354 A1 | 10/2012 | Kellett |
| 2012/0277842 A1 | 11/2012 | Kunis |
| 2012/0289988 A1 | 11/2012 | Riina et al. |
| 2012/0289994 A1 | 11/2012 | Larson et al. |
| 2012/0316584 A1 | 12/2012 | Miles et al. |
| 2012/0330347 A1 | 12/2012 | Becking et al. |
| 2012/0330348 A1 | 12/2012 | Strauss et al. |
| 2013/0053879 A1 | 2/2013 | Gailloud et al. |
| 2013/0102996 A1 | 4/2013 | Strauss |
| 2013/0103074 A1 | 4/2013 | Riina et al. |
| 2013/0109987 A1 | 5/2013 | Kunis et al. |
| 2013/0116774 A1 | 5/2013 | Strauss et al. |
| 2013/0123899 A1 | 5/2013 | Leopold et al. |
| 2013/0178889 A1 | 7/2013 | Miles et al. |
| 2013/0204282 A1 | 8/2013 | Nelson |
| 2013/0204311 A1 | 8/2013 | Kunis |
| 2013/0289714 A1 | 10/2013 | Strauss et al. |
| 2014/0128780 A1 | 5/2014 | Kennedy et al. |
| 2014/0222059 A1 | 8/2014 | Leopold et al. |

FOREIGN PATENT DOCUMENTS

| | | |
|---|---|---|
| EP | 1188413 | 3/2002 |
| EP | 1317908 A2 | 6/2003 |
| EP | 1600110 | 11/2005 |
| EP | 1707233 A2 | 10/2006 |
| EP | 1752112 | 2/2007 |
| EP | 1813196 | 8/2007 |
| EP | 1820436 A2 | 8/2007 |
| EP | 1852073 | 11/2007 |
| EP | 2248471 A1 | 11/2010 |
| EP | 2366362 | 9/2011 |
| EP | 2366363 | 9/2011 |
| EP | 2366364 | 9/2011 |
| EP | 2404580 | 1/2012 |
| EP | 2583636 | 4/2013 |
| GB | 2404860 A | 2/2005 |
| GB | 2494820 A | 3/2013 |
| JP | 07-18501 | 7/1995 |
| JP | 2010-532180 A | 10/2010 |
| JP | 2012-525859 A | 10/2012 |
| WO | WO-83/00997 A1 | 3/1983 |
| WO | WO-92/14408 | 9/1992 |
| WO | WO-94/00179 A1 | 1/1994 |
| WO | WO-95/24158 | 9/1995 |
| WO | WO-95/32018 | 11/1995 |
| WO | WO-96/18361 | 6/1996 |
| WO | WO-97/13463 A1 | 4/1997 |
| WO | WO-97/13471 A1 | 4/1997 |
| WO | WO-97/27893 | 8/1997 |
| WO | WO-97/27897 A1 | 8/1997 |
| WO | WO-97/27898 | 8/1997 |
| WO | WO-97/31672 A1 | 9/1997 |
| WO | WO-98/08456 A1 | 3/1998 |
| WO | WO-98/31308 | 7/1998 |
| WO | WO-98/34546 | 8/1998 |
| WO | WO-98/46115 A2 | 10/1998 |
| WO | WO-98/46119 A1 | 10/1998 |
| WO | WO-99/12484 A1 | 3/1999 |
| WO | WO-99/23976 A1 | 5/1999 |
| WO | WO-99/25273 A1 | 5/1999 |
| WO | WO-99/48545 A1 | 9/1999 |
| WO | WO-99/49793 A1 | 10/1999 |
| WO | WO-99/49910 A2 | 10/1999 |
| WO | WO-99/62430 A1 | 12/1999 |
| WO | WO-00/09195 | 2/2000 |
| WO | WO-00/16847 A1 | 3/2000 |
| WO | WO-00/27303 A2 | 5/2000 |
| WO | WO-00/67671 A1 | 11/2000 |
| WO | WO-01/32254 A1 | 5/2001 |
| WO | WO-01/80776 A1 | 11/2001 |
| WO | WO-01/80777 A2 | 11/2001 |
| WO | WO-01/89413 A2 | 11/2001 |
| WO | WO-02/03889 | 1/2002 |
| WO | WO-03/001970 A2 | 1/2003 |
| WO | WO-03/073961 A1 | 9/2003 |
| WO | WO-03/073962 A1 | 9/2003 |
| WO | WO-03/101518 A1 | 12/2003 |
| WO | WO-2004/006804 A1 | 1/2004 |
| WO | WO-2004/073557 A2 | 9/2004 |
| WO | WO-2005/020786 A2 | 3/2005 |
| WO | WO-2005/092241 | 10/2005 |
| WO | WO-2005/117755 A2 | 12/2005 |
| WO | WO-2006/017470 A2 | 2/2006 |
| WO | WO-2006/028943 A1 | 3/2006 |
| WO | WO-2006/031602 A1 | 3/2006 |
| WO | WO-2006/034153 A2 | 3/2006 |
| WO | WO-2006/074163 A2 | 7/2006 |
| WO | WO-2006/096342 A1 | 9/2006 |
| WO | WO-2006/111801 A2 | 10/2006 |
| WO | WO-2006/134354 A1 | 12/2006 |
| WO | WO-2007/061927 A2 | 5/2007 |
| WO | WO-2007/070544 A2 | 6/2007 |
| WO | WO-2007/085373 | 8/2007 |
| WO | WO-2007/127351 A1 | 11/2007 |
| WO | WO-2008/010197 A2 | 1/2008 |
| WO | WO-2008/100790 A2 | 8/2008 |
| WO | WO-2008/112501 A2 | 9/2008 |
| WO | WO-2008/153653 | 12/2008 |
| WO | WO-2009/064618 A1 | 5/2009 |
| WO | WO-2009/077845 A2 | 6/2009 |
| WO | WO-2009/088905 A1 | 7/2009 |
| WO | WO-2009/124288 | 10/2009 |
| WO | WO-2009/126747 | 10/2009 |
| WO | WO-2010/009019 | 1/2010 |
| WO | WO-2010/047644 | 4/2010 |
| WO | WO-2010/075565 A2 | 7/2010 |
| WO | WO-2010/085344 A1 | 7/2010 |
| WO | WO-2010/096717 A1 | 8/2010 |
| WO | WO-2010/130617 | 11/2010 |
| WO | WO-2010/146581 | 12/2010 |
| WO | WO-2010/148246 A2 | 12/2010 |
| WO | WO-2011/011581 A2 | 1/2011 |
| WO | WO-2011/153304 | 12/2011 |
| WO | WO-2011/163157 A2 | 12/2011 |
| WO | WO-2012/002944 A1 | 1/2012 |
| WO | WO-2012/040380 | 3/2012 |
| WO | WO-2012/067724 A1 | 5/2012 |
| WO | WO-2012/109367 | 8/2012 |
| WO | WO-2012/111137 | 8/2012 |

(56) References Cited

FOREIGN PATENT DOCUMENTS

| WO | WO-2012/131672 A2 | 10/2012 |
|---|---|---|
| WO | WO-2012/134761 | 10/2012 |
| WO | WO-2012/135859 A2 | 10/2012 |
| WO | WO-2012/166804 | 12/2012 |
| WO | WO-2013/055703 A1 | 4/2013 |
| WO | WO-2013/059511 A1 | 4/2013 |
| WO | WO-2013/067299 | 5/2013 |

OTHER PUBLICATIONS

International Search Report and Written Opinion dated Jul. 8, 2014, which issued in International Application No. PCT/US2013/076964.
U.S. Appl. No. 14/281,797, filed May 19, 2014.
Aydogan, Transcatheter Embolization Treatment of Coronary Arteriovenous Fistulas, Asian Cardiovascular & Thoracic Annals, 2003, pp. 63-67, vol. 11, No. 1.
Berguer et al., Cure by Combination of Operation and Detachable Intravascular Balloon, Ann. Surg. Jul. 1982, pp. 65-68, vol. 196, No. 1.
Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.
DeSouza et al., Embolization with Detachable Balloons—Applications Outside the Head, Clinical Radiology, Apr. 21, 1992, pp. 170-175, vol. 46.
Ferro et al, Percutaneous Transcatheter Embolization of a Large Pulmonary Arteriovenous Fistula with an Amplatzer Vascular Plug, Cardovacs Intervent Radiol, 2007, pp. 328-331, vol. 30.
Hawkins et al., The Permeability of Detachable Latex Rubber Balloons—An In Vitro Study, Investigative Radiology, Dec. 1987, pp. 969-972, vol. 22.
Hirai et al., Emergency Balloon Embolization for Carotid Artery Rupture Secondary to Postoperative Infection, Cardiovasc Intervent Radiol, 1996, pp. 50-52, vol. 19.
Kadir et al., Therapeutic Embolization of the Kidney with Detachable Silicone Balloons, The Journal of Urology, Jan. 1983, pp. 11-13, vol. 129.
Kallmes et al., The Use of Hydrocoil for Parent Artery Occlusion, AJNR Am J Neuroradiol, Sep. 2004, pp. 1409-1410, vol. 25.
Kaufman, et al., Detachable Balloon-Modified Reducing Stent to Treat Hepatic Insufficiency After Transjugular Intrahepatic Portosystemic Shunt Creation, J Vasc Intery Radiol., May 2003, pp. 635-638, vol. 14, No. 5.
Luo, Chao-Bao et al., Endovascular Treatment of the Carotid Artery Rupture with Massive Hemorrhage, J. Chin Med Assoc., Mar. 2003.
Makita, et al., Guide-Wire-directed Detachable Balloon: Clinical Application in Treatment of Varicoceles, Radiology, 1992, pp. 575-577, vol. 183.
Marshall et al., Treatment of Traumatic Renal Arteriovenous Fistulas by Detachable Silicone Balloon Embolization, The Journal of Urology, Aug. 1979, pp. 237-239, vol. 122.
Pollak et al., Clinical Results of Transvenous Systemic Embolotherapy with a Neuroradiologic Detachable Balloon, Radiology, May 1994, pp. 477-482, vol. 191, No. 2.
Reidy et al., Transcatherer Occlusion of Coronary to Bronchial Anastomosis by Detachable Balloon Combined with Coronary Angioplasty at Same Procedure, Brit Heart J. 1983, pp. 284-287, vol. 49.
Reidy et al., Transcatheter Occlusion of a Blalock-Taussig Shunt with a Detachable Balloon in a Child, Bri Heart Journal, 1983, pp. 101-103, vol. 50.
Ross et al., The Vascular Plug: A New Device for Parent Artery Occlusion, AJNR Am J Neuroradiol, Feb. 2007, pp. 385-386, vol. 28.
Serbinenko, F.A., Balloon Catheterization and Occlusion of Major Cerebral Vessels, J. Neurosurg. Aug. 1974, pp. 125-145, vol. 41.
Tasar, et al., Intrahepatic Arterioportal Fistula and its Treatment with Detachable Balloon and Transcatheter Embolization with Coils and Microspheres, Journal of Clinical Imaging, 2005, pp. 325-330, vol. 29.
Wehman, et al., Giant Cerebral Aneurysms: Endovascular Challenges, Neurosurgery, Nov. 2006, pp. S125-S138, vol. 59, No. 5.
White, et al., Occlusion of Varicoceles with Detachable Balloons, Radiology, May 1981, pp. 327-334, vol. 139.
Serbinenko, F.A., Occlusion by Balooning of Sacular Aneurysms of the Cerebral Arteries, Vopr, Neirokhir, Jul.-Aug. 1974, pp. 8-15, vol. 4.
Serebinko, F.A., Balloon Occlusion of Cavernous Portion of the Carotid Artery as a Method of Treating Carotid Cavity Anastomoses, Vopr. Neirokhir, Nov.-Dec. 1971, pp. 3-9, vol. 6.
Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.
U.S. Appl. No. 14/044,794, filed Oct. 2, 2013.
U.S. Appl. No. 14/101,171, filed Dec. 9, 2013.

* cited by examiner

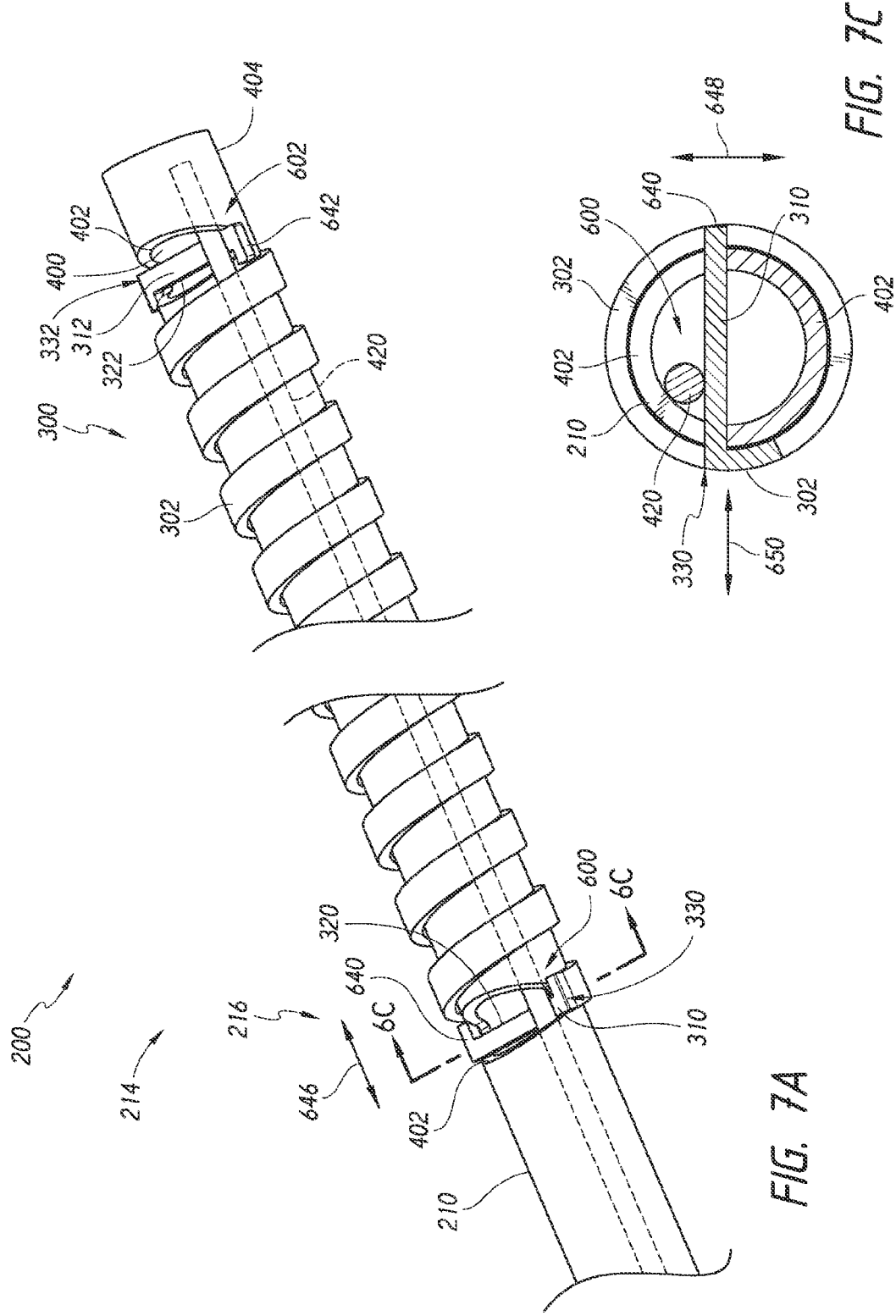

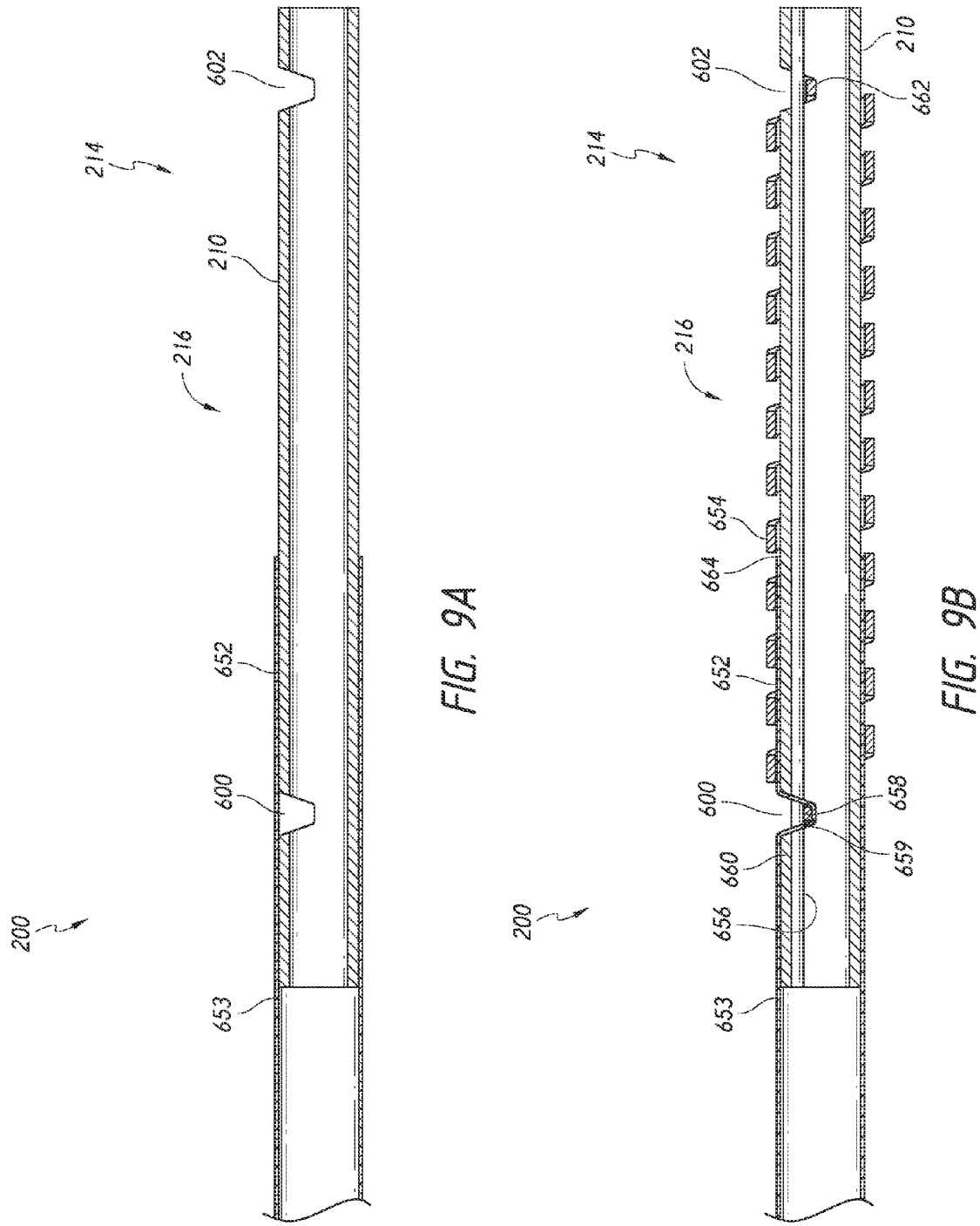

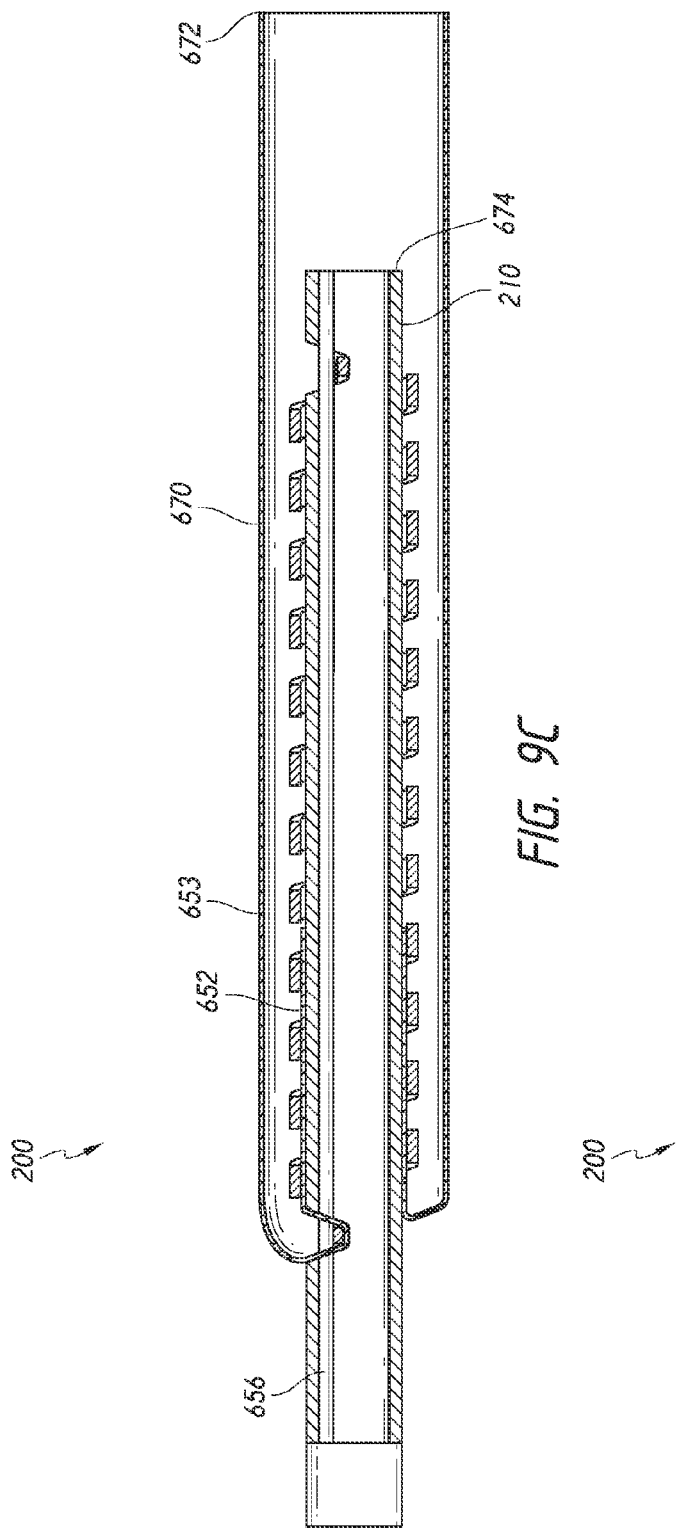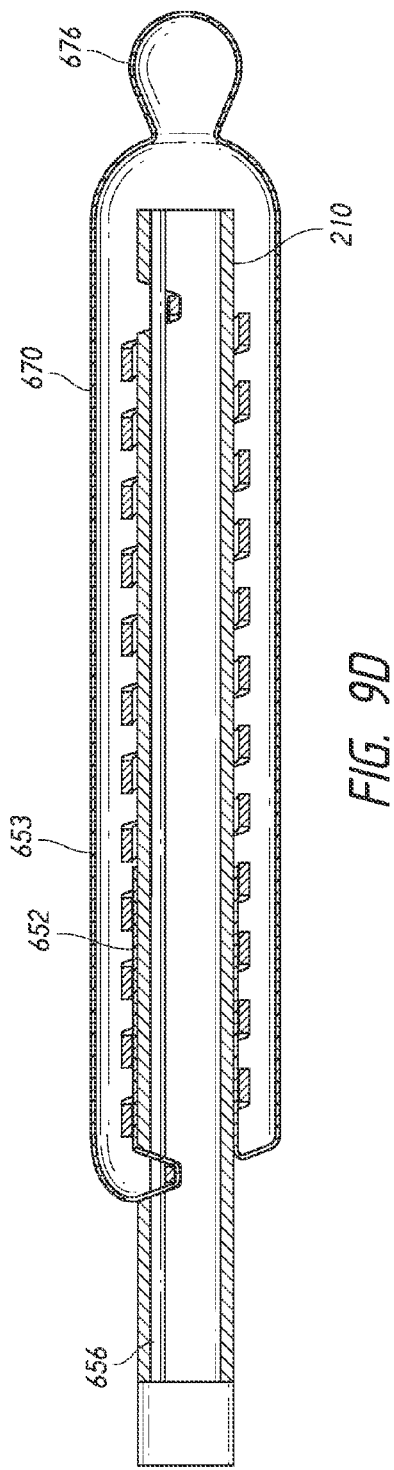

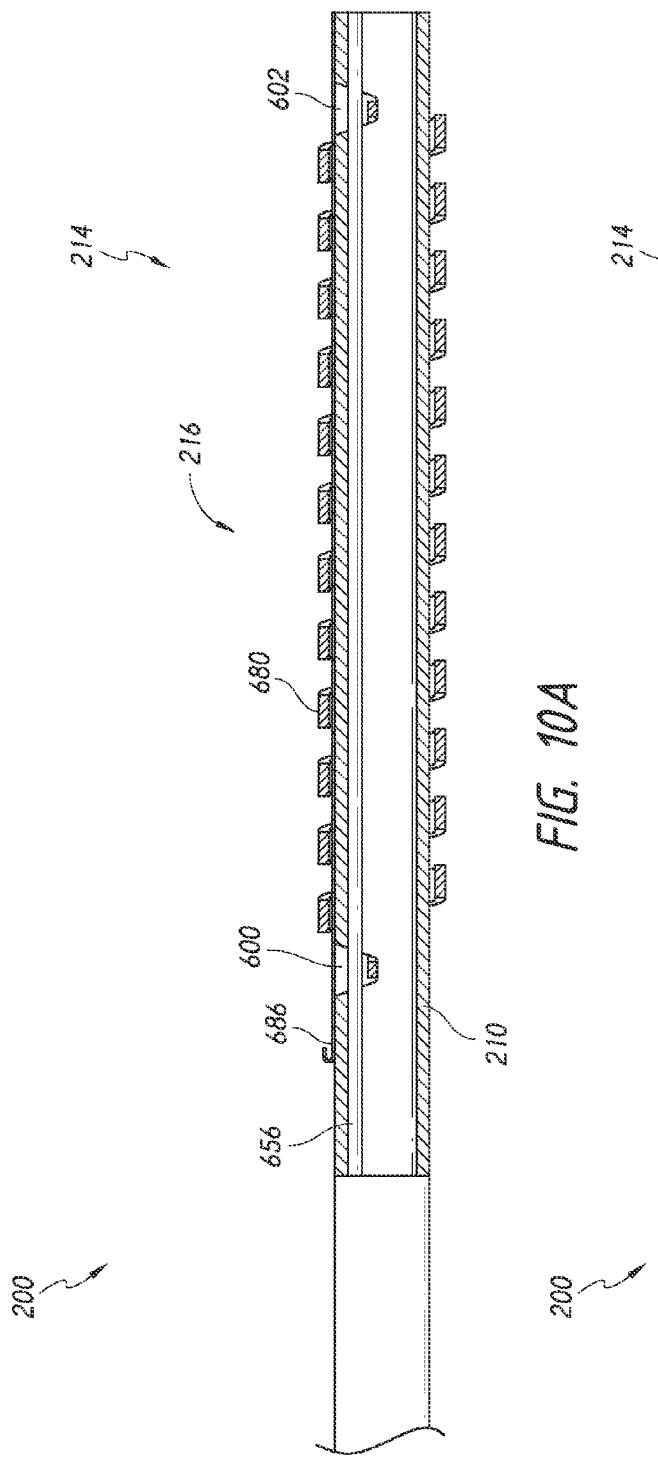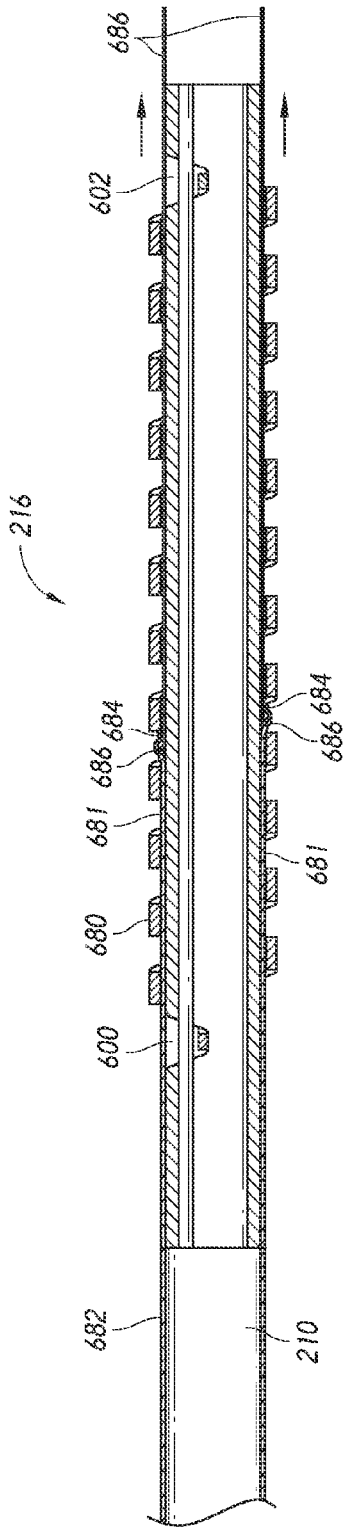

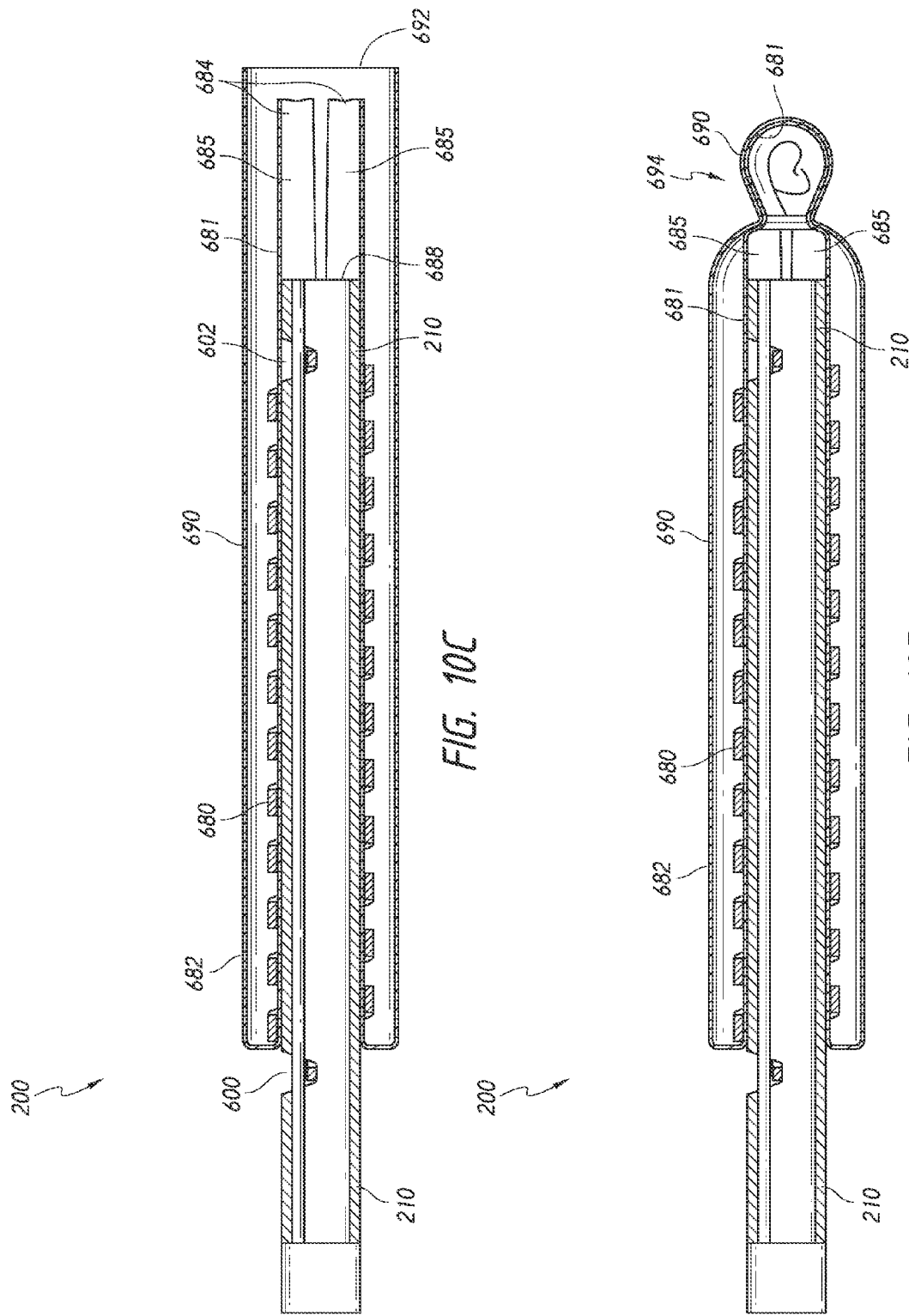

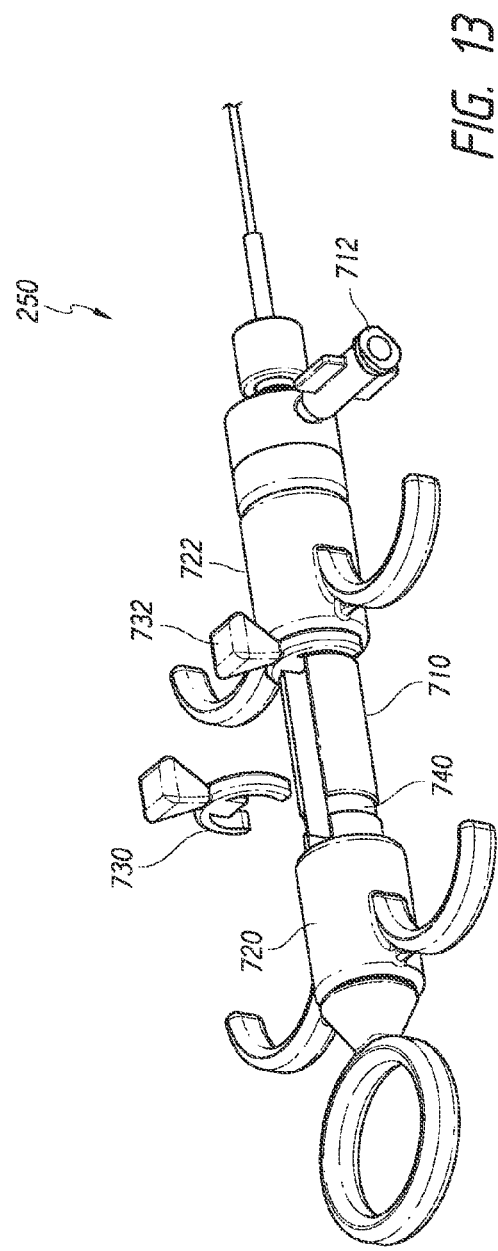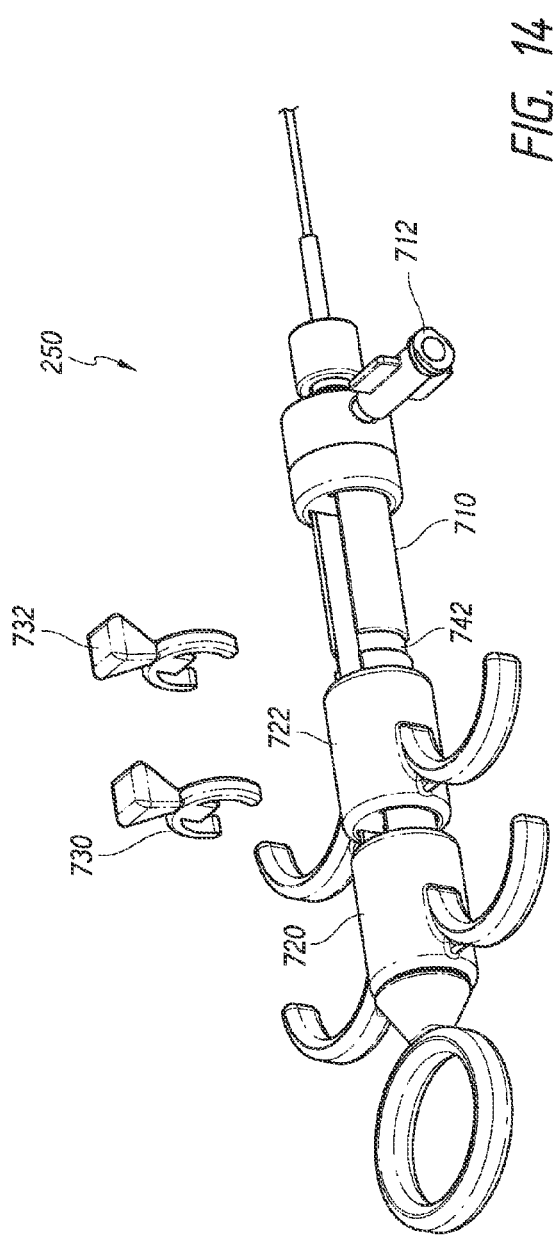

BODILY LUMEN OCCLUSION

CROSS-REFERENCE TO RELATED APPLICATIONS

This application is a continuation-in-part of U.S. patent application Ser. No. 13/828,974, filed on Mar. 14, 2013, which claims the priority benefit of U.S. Provisional Application No. 61/761,195, filed Feb. 5, 2013, the entirety of each of which is incorporated herein by reference.

BACKGROUND

1. Field of the Inventions

The subject technology relates generally to bodily lumen occlusion, and in some aspects, to endoluminal occlusion systems and their methods of use.

2. Description of the Related Art

Rapid, well-controlled, and safe methods to limit bleeding in vessels have encouraged the development of endovascular devices and techniques, and their introduction into clinical practice. Early devices used balloons, either non-detachable or later detachable, in order to block vessels, for example, in the treatment of carotid-cavernous fistulas and saccular aneurysms.

Typically made from latex or silicone, balloons are delivered to a desired location in a vessel, and then inflated in order to physically occlude the vessel. While other devices have since been developed, balloon occlusion remains in use, and is indicated for use in treating a variety of life-threatening conditions, including for example, giant cerebral and skull base aneurysms, traumatic and non-traumatic vessel injury or rupture, vertebro-vertebral arteriovenous fistulas, and pre-operative tumor resections.

Detachable balloons are also useful clinically in procedures outside of neurological intervention. For example, balloons can be useful in flow reduction procedures such as shunt occlusion in patients with transjugular intrahepatic portosystemic shunts and hepatic insufficiency, intrahepatic arterioportal fistulas, treatment of varicoceles, shunt occlusion in patients with a Blalock-Taussig shunt, obliteration of pulmonary arteriovenous fistulas, arteriovenous malformations or aortopulmonary anastomoses, coronary arteriovenous fistulas, or renal arteriovenous fistulas. Detachable balloons are also used in preoperative devascularization before surgical resection of organs such as the kidney.

SUMMARY

Despite their usefulness, balloon occlusion devices suffer from limitations that affect their ease of use and safety. By its very nature, a balloon can expand and rupture, or alternatively it can spontaneously deflate over time. Deflation is more common with latex balloons, with some studies reporting 100% deflation rates. Spontaneous deflation can result in treatment failure and reoccurrence of the lesion.

Detachable balloon devices present other problems as well, and their use in the intracranial vasculature presents specific challenges. For example, balloons lack trackability, meaning that they are difficult to navigate, especially through tortuous vessels, such as those commonly found in the intracranial circulation. In addition, premature (i.e., non-intentional) detachment from the delivery device can lead to adverse consequences such as cerebral artery blockage and stroke.

Even once in place they typically move forward during the process of inflation, making placement of the unexpanded balloon in order to achieve precise positioning after inflation relatively difficult. Balloons that dislodge and migrate can require open skull surgery especially where the balloon has become lodged in a major vessel, for example, in a cerebral artery.

More recently, detachable balloons have become unavailable for use in the United States. Further, silicone balloons were retired from the market several years ago, and the only alternative, the Goldvalve™ latex balloon, is difficult to obtain, and its use carries the risk of adverse reaction in patients allergic to latex. Thus, a vacuum exists in the field of vessel occlusion therapies, and consequently, interventionalists are left with few options to perform vessel occlusion procedures.

One approach has been to use hydrogel-coated coils in order to produce rapid vascular occlusion. However, there still remains a significant period of time between placement of the coil, and formation of the occlusive clot, even when using coated coils. This leads to concern that during formation of the clot, distal clot migration can occur, with potentially devastating consequences such as stroke. Further, the geometric configuration and unpredictability of coil-based embolization prevents precise occlusion of a short vascular segment. The risk of distal migration of a clot is also of concern when treating high-flow peripheral lesions such as pulmonary arteriovenous fistulas.

The Amplatzer® Vascular Plug, a device made of a self-expanding Nitinol mesh, can be used to block flow through a vessel by inducing formation of a clot. However, as discussed above, this device is unable to provide for acute occlusion therapy and thus the risk of distal clot migration into remains. The device is also limited by it navigability, and placement precision, which limits its utility to use in performing occlusions below the base of the skull.

As a result of the limitations in prior art apparatus and methods for occluding vessels, the present disclosure recognizes that it is desirable to provide an apparatus and method that effectively provides acute blockage of a desired vessel, or alternatively, limited flow through a vessel, is relatively easy to place and deploy, and which will be stable over time, while avoiding limitations and problems inherent in the prior art apparatus and methods.

Accordingly, many conditions, including pelvic venous incompetence, create the need to close blood vessels that have lost their integrity. There a number of treatments aimed at closing these dilated veins, but even the most highly recommended procedure, microcoil embolization, involves deploying a large amount of permanent metallic coils within the body, as shown in FIG. 1. In this procedure, a coil 10 is inserted into a luminal space 20 in order to reduce or block flow through the luminal space 20. Generally, this procedure also involves exposure, and often prolonged exposure, to x-ray radiation. This can be harmful to patients, especially those of childbearing age.

Embodiments of the systems and devices disclosed herein address the unmet need for a device that can provide a fast, precise and reliable way to close a bodily lumen. The endoluminal occlusion system can include two major subsystems: a guide sheath assembly and an implant carrier assembly. The implant carrier assembly can include an implant device and a handle assembly. Embodiments of the present disclosure can also comprise various features disclosed in U.S. Pat. No. 8,328,840, issued on Dec. 11, 2012, entirety of which is incorporated herein by reference.

In accordance with some embodiments, a guide sheath assembly can be provided that comprises a guide sheath and a removable core. The guide sheath and the removable core can be advanced into a bodily lumen or vessel until reaching a target region. The guide sheath can have a lumen that is configured to receive the removable core therein. The removable core can also have a lumen that is configured to receive a guide wire therethrough. Thus, the removable core and the guide sheath can be advanced over the guide wire until reaching the target region of the bodily lumen or vessel. Once the guide sheath assembly is in place at the target region, the removable core can be removed, along with the guide wire, from the bodily lumen or vessel. At this stage, the guide sheath can remain placed at the target region.

The implant carrier assembly can be configured to be inserted into the lumen of the guide sheath. The implant carrier assembly can comprise a catheter that is attached to the handle assembly at a proximal end of the catheter. The catheter can also define a distal end that is configured to support the implant thereon.

The handle assembly can comprise one or more actuator members that can be actuated to selectively release or disengage at least a portion of the implant from the distal end of the catheter. In some embodiments, the actuator member(s) can comprise a slider or pull member.

The slider or pull member can be coupled to a handle frame component. The handle frame component can be coupled to the catheter and provide a generally fixed spatial relationship relative to the distal end of the catheter and the handle frame component. Thus, according to some embodiments, the slider or pull member can move relative to the distal end of the catheter.

In some embodiments, the slider or pull member can be coupled to an elongate wire that extends from the slider or pull member to the distal end of the catheter. Accordingly, when the slider or pull member is proximally retracted, a proximal retracting force is exerted upon the wire, which can result in disengagement of the implant from the distal end of the catheter. The elongate wire can have a diameter of from about 0.005 inches to about 0.008 inches. The presence of wires in the catheter can advantageously provide column strength for the implant carrier assembly.

In some embodiments, the handle assembly can comprise two or more actuator members, such as sliders or pull members. Further, the handle assembly can also comprise wires coupled to the sliders or pull members. The sliders or pull members can be coupled to the elongate wires that extend within a lumen of the catheter. For example, the handle assembly can have two actuator members and two wires.

The distal end of the catheter can comprise an engagement seat or section that is configured to receive and facilitate engagement with at least a portion of the implant to maintain the implant engaged with the distal end of the catheter.

The engagement section can be configured to facilitate engagement between the implant and a wire extending from the handle assembly. In some embodiments, the engagement section can facilitate engagement between the implant and two or more wires extending from the handle assembly.

In some embodiments, the engagement section or seat can comprise at least one engagement component, such as a protrusion, aperture, slot, opening, or notch. The protrusion, aperture, slot, opening, or notch can be disposed on an outer surface of the engagement section or extend inwardly to a lumen of the catheter from an outer surface of the engagement section. At least a portion of the implant can be engaged with the protrusion, aperture, slot, opening, or notch. For example, the engagement section can comprise a generally tubular member having a lumen. At least a portion of the implant can be received into the protrusion, aperture, slot, opening, or notch and be engaged with a member, such as an elongate member or wire, extending along or through the engagement section. For example, the implant can be disposed on the engagement section, such as by being wound about the engagement section.

In some embodiments, a flattened portion of the implant extending across the aperture within the catheter lumen. A wire can lock the flattened portion radially within the engagement section aperture to prevent movement between the implant and the engagement section.

In some embodiments, the flattened portion of the implant can comprise a notch, cut-out, or indentation. The notch can be received within the aperture of the engagement section. Thus, when the elongate member is positioned so as to lock the flattened portion radially within the aperture, the notch of the flattened portion can secure the flattened portion relative to the aperture of the engagement section to prevent the flattened portion from sliding out of the engagement section aperture.

The handle assembly can also comprise a fluid inlet for providing fluid to the distal end of the catheter. The distal end of the catheter can comprise one or more apertures or perforations for permitting the passage of fluid into the implant for flushing the device.

In use, in accordance with some embodiments, once guided to the vascular area to be closed, the sheath can be adjusted precisely to obtain optimal position within the vessel. The removable core and guide wire can then be taken out of the guiding sheath, and the implant carrier is advanced through the sheath. The proximal end of the device is released first, followed by the distal end. The device's membrane or cover member can be filled with incoming blood, helping the device to be secured against the vessel wall.

In order to release the device, according to some embodiments, the operator can remove the first clip from the handle assembly and then pulls the proximal slider to release the proximal end of the device. The second clip can then be removed from the handle assembly and the distal slider can be pulled to release the distal end of the device.

For example, in some embodiments, an occlusion device delivery system is provided that can comprise a catheter, and expandable coiled implant, and an elongate member. The catheter can have a lumen extending between distal and proximal portions. The distal portion can have proximal and distal apertures extending through a wall of the catheter. The expandable coiled implant can be wound about the distal portion. Further, the implant can have a proximal section that extends within the proximal aperture and a distal section that extends radially within the distal aperture. The elongate member can extend through the catheter lumen and engaging and radially restrain the at least one of the proximal or distal sections within its respective aperture while engaged with the member.

In some embodiments, the implant, when coiled about the distal portion, can comprise a lumen and at least one of the proximal or distal sections can extend across the implant lumen. Further, when the implant is coiled about the distal portion in some embodiments, the implant can extend between the proximal and distal apertures along a generally helical path and at least one of the proximal or distal sections can then radially inwardly from the helical path.

An occlusion implant or device can also be provided in some embodiments. The occlusion implant can comprise a helical member, support member, scaffold, or wire supporting a generally impermeable membrane or cover member. The member can be braided or comprise a single helical member. The occlusion implant can have proximal and distal sections. The device proximal end section can be open and the distal section can be closed to prevent passage of fluid through the implant. The implant can comprise any of the various features discussed herein.

The occlusive device proximal and distal sections can extend across the catheter lumen. The proximal and distal sections can extend across the catheter lumen less than a diameter of the catheter lumen.

In some embodiments, the elongate member can extend through the catheter lumen and between at least one of the proximal or distal sections of the occlusive device and its respective aperture, outer surface, or wall of the catheter. Upon proximal withdrawal of the elongate member through the catheter lumen, the elongate member can be configured to disengage and radially release the at least one of the proximal or distal sections of the occlusive device from its respective aperture. Further, in some embodiments, the elongate member can engage both the proximal and distal sections of the occlusive device. The elongate member can comprise a wire.

In some embodiments, the at least one of the proximal or distal sections of the occlusive device can have a respective end that is configured to extend radially out of its respective aperture while engaged with the elongate member. Further, the respective end can be larger than the respective section extending through the aperture. Thus, the respective end and the respective section of the occlusive device can engage the respective aperture such that the respective section is generally restrained from movement transverse to an axis of the catheter when the elongate member is engaged with and radially restraining the respective section within the respective aperture.

For example, the occlusive device proximal section can be configured to comprise a reduced cross-sectional segment that is configured to extend within the proximal aperture. The reduced cross-sectional segment can be configured to extend within the distal aperture while the implant is coiled about the distal portion. Further, the reduced cross-sectional segment can comprise a notch, cut-out, or indentation. For example, in some embodiments, the notch, cut-out, or indentation and the aperture can each have substantially equal lengths, transverse to an axis of the catheter lumen, and be configured to engage each other. Further, the apertures can comprise slots that are transverse to an axis of the catheter lumen. Thus, the notch, cut-out, or indentation of a section of the occlusive device can extend transversely across an aperture of the catheter engagement section and be and be restrained from movement transverse to an axis of the catheter when the elongate member is engaged with and radially restraining the device section within the respective aperture.

A handle assembly can also be provided for selectively releasing an intravascular implant device, the handle assembly having first and second sliders and first and second clips. The first and second clips can prevent movement of the first and second sliders and being removable from the handle assembly to permit movement of the first and second sliders. The first slider can be operative to disengage an implant device proximal end from the catheter. The second slider can be operative to disengage an implant device distal end from the catheter.

In some embodiments, a method of deploying an occlusion device in a blood vessel is provided. The method can comprise the steps of: advancing a catheter in a blood vessel to position an expandable coiled implant, wound about a distal portion of the catheter, the distal portion having proximal and distal apertures extending through a wall of the catheter, the implant having a proximal section that extends within the proximal aperture and a distal section that extends within the distal aperture; and proximally withdrawing an elongate member extending through a lumen of the catheter to proximally withdraw the elongate member through the catheter lumen.

The method can be implemented to further comprise the steps of: removing a first clip from a handle assembly to permit movement of a first slider of the handle assembly to proximally withdraw the elongate member; and proximally retracting the first slider to disengage and radially release the at least one of the implant proximal or distal sections from its respective aperture.

Further, when the implant proximal section is engaged and radially restrained by the elongate member and the implant distal section can be engaged and radially restrained by a second elongate member extending through the catheter lumen. In some embodiments, the method can further comprise proximally withdrawing the second elongate member to disengage and radially release the implant distal section from its respective aperture.

The method can also comprise positioning a guide sheath at a treatment site and unsheathing an occlusion implant from the guide sheath. The implant can have proximal and distal sections that are engaged with a catheter. The catheter being operatively interconnected with a handle assembly for selectively controlling engagement and release of the implant with the catheter.

The method can also be implemented to comprise the steps of: removing a second clip from the handle assembly to permit movement of a second slider of the handle assembly; and proximally retracting the second slider to proximally withdraw the second elongate member. The steps of removing a second clip and proximally retracting the second slider can be performed after the first slider has been proximally retracted. The method can also be implemented such that the steps of removing a second clip and proximally retracting the second slider are performed after the first slider has been proximally retracted.

Some embodiments can also provide an occlusion device delivery system that comprises a microcatheter, a removable core, and an implant assembly. The removable core can extend along an inner lumen of the microcatheter. The implant assembly can comprise a catheter, an occlusion device, and a handle assembly. The catheter can have a proximal end and a distal end. The occlusion device can be coupled to the catheter distal end. The occlusion device can have a helical member, support member, or wire supporting a generally impermeable membrane or cover member. The occlusion device can have proximal and distal ends. The handle assembly can have first and second sliders and first and second clips. The first and second clips can prevent movement of the first and second sliders and can be removable from the handle assembly to permit movement of the first and second sliders. The first slider can be operative to disengage the device proximal end from the catheter. The second slider can be operative to disengage the device distal end from the catheter.

In some embodiments, the system can be configured such that the catheter comprises first and second apertures. Further, the support member of the occlusion device can comprise first and second portions that fit into the first and second apertures.

The handle assembly can further comprise first and second wires coupled to the first and second sliders. The first and second wires can extend distally to engage with the first and second portions of the occlusion device to radially restrain the first and second portions of the occlusion device in the respective first and second apertures.

In accordance with yet other embodiments, methods of manufacturing an occlusive device are also disclosed herein.

The method can comprise the steps of: positioning or securing a support member over an engagement section of a catheter, and attaching a cover member to the support member. The features of other embodiments disclosed herein can also be implemented in methods of manufacturing the occlusive device. For example, the support member can be self-expanding and can be compressed or wound onto the engagement section of the catheter, which can be along a distal portion of the catheter. The support member can be secured to the engagement section by engaging one or both end portions of the support member relative to the catheter distal end. For example, one or both end portions of the support member can be inserted into respective apertures in the engagement section to engage with one or more elongate members or wires. The engagement between the elongate member(s) and the end portion(s) of the support member can enable the device to be maintained in a collapsed configuration on the catheter and subsequently expanded.

The method of manufacturing the device can be implemented by positioning a first end portion of the cover member over the engagement section prior to positioning or securing the support member over the engagement section. Further, a second end portion of the cover member can be everted over the first end portion of the cover member, and an end of the second end portion of the cover member can be closed to form a closed end of the occlusive device.

In embodiments in which the cover member is placed over the engagement section prior to positioning or securing the support member, the support member can be positioned such that it covers the first end portion of the cover member. For example, the support member can be positioned over the engagement section such that the cover member first end portion is interposed between the support member and the engagement section.

In some embodiments, the method can be implemented by positioning the first end portion of the cover member over an aperture in the engagement section prior to positioning or securing the support member over the engagement section. An end portion of the support member can be inserted into the aperture in the engagement section to secure the support member to the engagement section. Thereafter, the second end portion of the cover member can be everted over the first end portion of the cover member, and the end portion of the second end portion of the cover member can be closed to form the closed end of the occlusive device.

In some embodiments, the method can also be implemented such that an end portion of the support member is inserted into an aperture, notch, or slit in the engagement section of the catheter. An elongate member can be inserted into a lumen of the catheter. A portion of the elongate member can be interposed radially between the support member end portion and a wall of the catheter such that the support member end portion is engaged by the elongate member within the aperture.

Further, a notch of the support member end portion can be aligned with the catheter aperture for restraining movement of the support member end portion in a direction transverse to an axis of the catheter. For example, the catheter aperture can have a width extending transverse to the catheter axis, and the aperture width can be about equal to a width of the support member notch.

For example, in some embodiments, when positioning or securing the support member over the cover member, an end portion of the support member can be inserted into the aperture in the engagement section to secure the support member to the engagement section. When the support member end portion is inserted into the aperture, the support member end portion can urge a portion of the cover member first end portion into the aperture.

Furthermore, an elongate member can be advanced through the catheter toward the engagement section for securing the support member relative to the engagement section. The elongate member can be used to pierce the cover member first end portion. For example, the elongate member can be advanced within the engagement section adjacent to the aperture of the engagement section and can pierce the portion of the cover member end portion urged into the aperture. In addition, the elongate member can be engaged with the support member end portion. The engagement between the elongate member and the support member end portion can comprise positioning the elongate member within the aperture, radially between of the support member end portion and an outer surface of the catheter.

Additionally, the catheter can comprise two apertures and the method can further comprise inserting a second end portion of the support member into a second aperture of the catheter. The method can also comprise engaging an elongate member with the support member second end portion in the second aperture. For example, an elongate member can be positioned within the second aperture, radially between of the support member second end portion and a wall of the catheter. The elongate member can be a first or a second elongate member. Thus, a first elongate member can be engaged with both the support member first and second ends, or the first elongate member can be engaged with the support member first end and the second elongate member can be engaged with the support member second end.

In some embodiments, the cover member can, in part or in its entirety, comprise a unitary or continuous tubular sleeve. In embodiments in which the cover member comprises a tubular sleeve, the catheter can be inserted into the cover member. The cover member can comprise an uninterrupted tube in both the first and second end portions of the cover member. However, the cover member first end portion can also comprise at least one extension member. The extension member can be flexible. The extension member can have a substantially rectangular shape. Further, the extension member can have a width that is greater than its length. Furthermore, the extension member can take the form of an elongate member such as a ribbon, wire, or strip of material. For example, an extension member of the first end portion can be coupled to an uninterrupted, tubular second end portion. Further, the cover member can be configured as a tube having one or more longitudinal slits that separate portions of the tube into one or more extension members. The cover member can comprise at least two, four, or eight extension members. For example, in some embodiments, the cover member can comprise two, three, four, five, six, seven, eight, or more extension members.

For example, in some embodiments, an occlusive implant device can be provided that comprises a support member and a cover member. The support member can be implantable in a body lumen to occlude flow through the lumen. The cover member can comprise first and second sections. The first section can extend around or about at least a portion of the support member and be engaged with the second section such that the cover member is secured to the support member. For example, the cover member can be secured to the support member without radially constraining the support member. The cover member can be coupled to and carried by the support member such that the cover member aids in disrupting or blocking flow through the body lumen.

According to some embodiments, the cover member can enclose the entire support member such that the support member is freely movable within the cover member. Ends of the cover member can be tied or joined to each other such that flow through the support member is disrupted or blocked.

For example, in some embodiments, the support member can comprise a tubular member, such as a helically extending wire. The cover member can comprise a tubular second portion that extends over an exterior or outer surface of the support member. The first section, which can extend from the second section, can be folded inverted, or otherwise inserted into a lumen of the support member. Respective ends of the first and second sections can be coupled to each other. For example, the respective ends of the first and second sections can be coupled to each other at an end of support member.

The cover member can be configured such that the first and/or second section comprises at least one extension member. For example, the first section of the cover member can comprise a plurality of extension members. The extension members can be created by cutting the first section or removing material from the first section. Thus, the extension members can be positioned immediately adjacent to each other or spaced apart from each other by a gap. The extension members of the first section can extend through the support member lumen and be coupled to an end of the second portion of the cover member.

Further, the method can be implemented by securing a support member to the engagement section prior to positioning the cover member at or along the engagement section. A wire can be positioned between the support member and the catheter. The wire can be placed against the catheter before the support member is secured to the engagement section. However, in some embodiments, the wire can be inserted between the support member and the engagement section in a proximal direction from a distal end portion of the support member. When in position, with a proximal end of the wire proximal to a proximal end of the support member, the wire can be attached to an extension member of a cover member. Thereafter, the wire can be pulled in a distal direction such that the extension member becomes positioned between the support member and the catheter.

In some embodiments, the method can be implemented using a plurality of wires. Each wire can be attached to one or more extension members of material. For example, in some embodiments, a plurality of extension members can be attached to a single wire.

After the extension member(s) of the cover member have been drawn distally through a space between the support member and the catheter engagement section by pulling the wire(s), the cover member second end portion can be everted over the support member.

After the cover member second end portion is everted over the support member (regardless of how the cover member first end portion has been positioned between the support member and the catheter engagement section), the cover member second end portion can be closed to close a distal end of the occlusive device. When closing the cover member second portion, the cover member second end portion can be sutured to the support member. Further, in embodiments in which the cover member first end portion comprises a plurality of extension members, the cover member second portion can be closed by coupling the extension members of the cover member first end portion and with the cover member second end portion.

Embodiments of the present system have the ability to close a bodily lumen or vessel rapidly and with confidence. This provides improved health and quality of life for millions of people.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIGS. 7A-7E illustrate aspects of an implant support member on a catheter distal section of an implant carrier assembly, according to some embodiments.

FIGS. 9A-9E illustrate views of a method of manufacturing an implant, according to some embodiments.

FIGS. 10A-10E illustrate views of another method of manufacturing an implant, according to some embodiments.

FIGS. 12-14 illustrate views of a handle assembly, according to some embodiments.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

While the present description sets forth specific details of various embodiments, it will be appreciated that the description is illustrative only and should not be construed in any way as limiting. It is contemplated that although particular embodiments of the present inventions may be disclosed or shown in particular contexts, such embodiments can be used in a variety of endoluminal applications. Various applications of such embodiments and modifications thereto, which may occur to those who are skilled in the art, are also encompassed by the general concepts described herein.

According to some embodiments, the systems and methods disclosed herein can be used for percutaneous, peripheral occlusion of the peripheral arterial and venous vasculature. For example, some embodiments can be used to treat pelvic venous incompetence, varicocele, gonadal vein for pelvic varices in females with chronic pelvic pain, stop blood loss from a damaged blood vessel due to a traumatic arterial injury, stop hemorrhage caused by a neoplasia, and close an abnormal blood vessel or blood vessels supplying a vascular anomaly such as arteriovenous malformations or arteriovenous fistulas, and other conditions. Other uses and applications of the system are provided in the appended documents.

Figure 1:
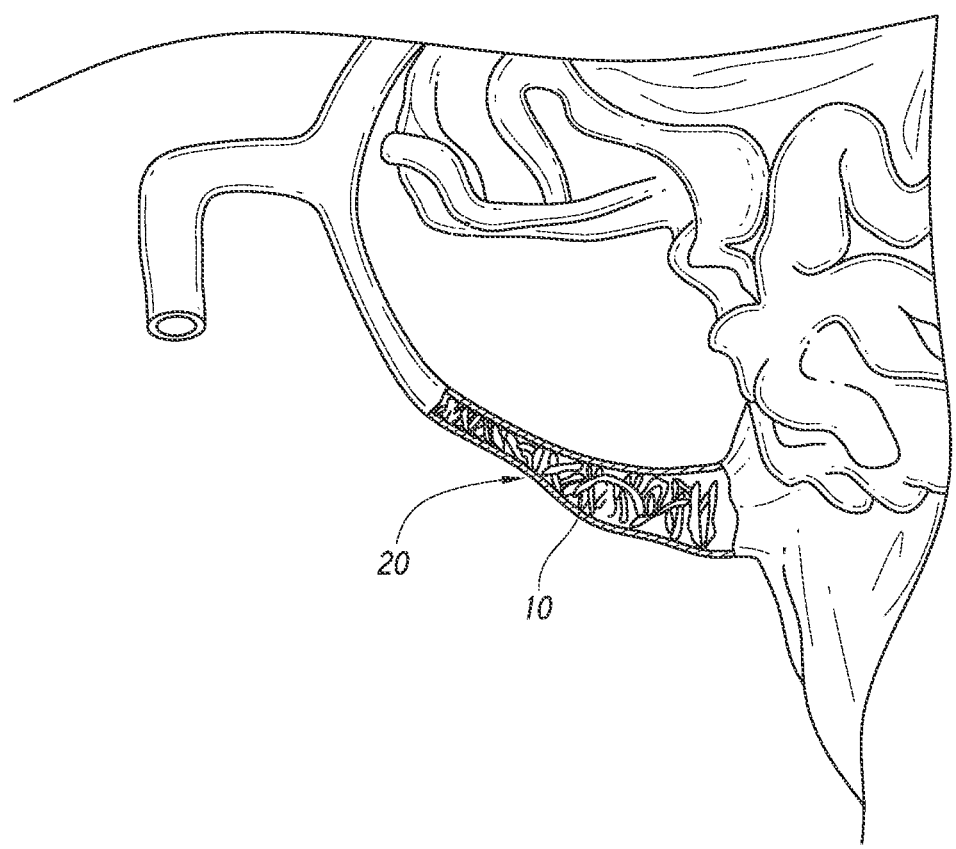
FIG. 1 is a schematic view of a body lumen having an occlusive coil disposed therein for treating pelvic venous incompetence.
Figure 2:
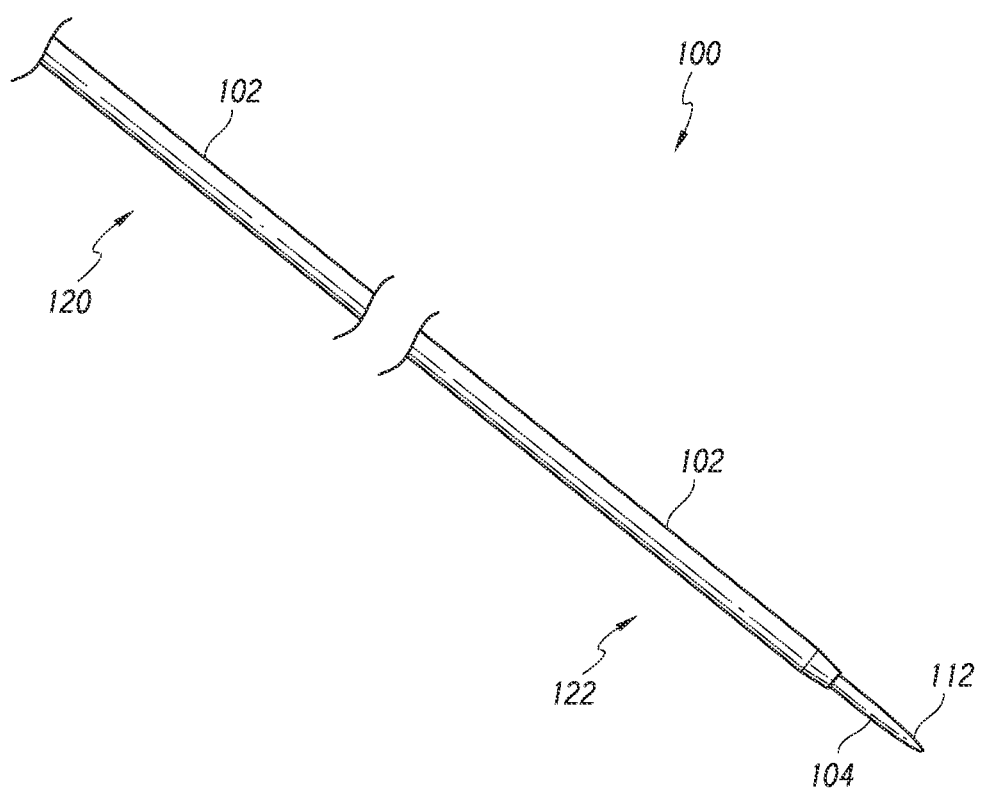
FIG. 2 is a top view of a guide sheath assembly, according to some embodiments.

Some embodiments comprise a guide sheath assembly that can be used to access a treatment site. The guide sheath assembly can be advanced to the treatment site, to deploy one or more devices, is disclosed herein. For example, FIG. 2 illustrates a guide sheath assembly 100 that comprises a guide sheath 102 and a removable core 104. In some embodiments, the guide sheath assembly 100 can be advanced over a wire to the treatment site. However, the guide sheath assembly 100 can also be configured to be advanced independently or without a wire.

The guide sheath assembly 100 can be configured such that the removable core 104 can fit inside a lumen of the guide sheath 102 and extend out of a distal end 110 of the sheath 102. The removable core 104 can comprise a distal tip 112 that can be configured to be atraumatic. For example, the distal tip 112 can be rounded (for example, in embodiments that are advanced over a wire) and/or comprise an atraumatic tip coil (for example, in embodiments that are advanced independently or without a wire).

The guide sheath 102 can comprise a braided shaft with a stiff proximal section 120 and a more flexible distal section 122 to enable tracking through tortuous peripheral vasculature. The guide sheath distal end 110 can be tapered and include a radiopaque marker that is visible under fluoroscopy.

In accordance with some embodiments, the total length of the guide sheath 102 can have a total length from about 40 cm to about 150 cm, from about 60 cm to about 120 cm, or from about 70 cm to about 90 cm. For example, in some embodiments, the total length of the guide sheath 102 can have a total length of about 80 cm. Further, some embodiments, the guide sheath 102 can have a working length from about 65 cm to about 110 cm, from about 75 cm to about 100 cm, or in some embodiments, about 89 cm.

Additionally, in some embodiments, the removable core can 104 have a lumen (not shown) through which a guidewire can extend and a tapered end 112 for ease of advancement into and through the blood vessel. The total length of the removable core 104 can be from about 50 cm to about 180 cm, from about 70 cm to about 150 cm, or in some embodiments, about 110 cm, with a working length of from about 85 cm to about 130 cm, from about 95 cm to about 120 cm, or in some embodiments, about 108 cm.

In order to place the guide sheath assembly 100 in a vessel of the body, a guide wire (having a diameter of 0.035") can be placed into the vessel, and the guide sheath 102 and removable core 104 can be advanced over the guide wire. The guide wire and removable core 104 can then be removed from the guide sheath 102 once the guide sheath 102 is in position for delivery of the implant.

After the guide sheath 102 is placed, an implant carrier assembly can be inserted into the guide sheath 102 and advanced to the treatment site.

Figure 3:
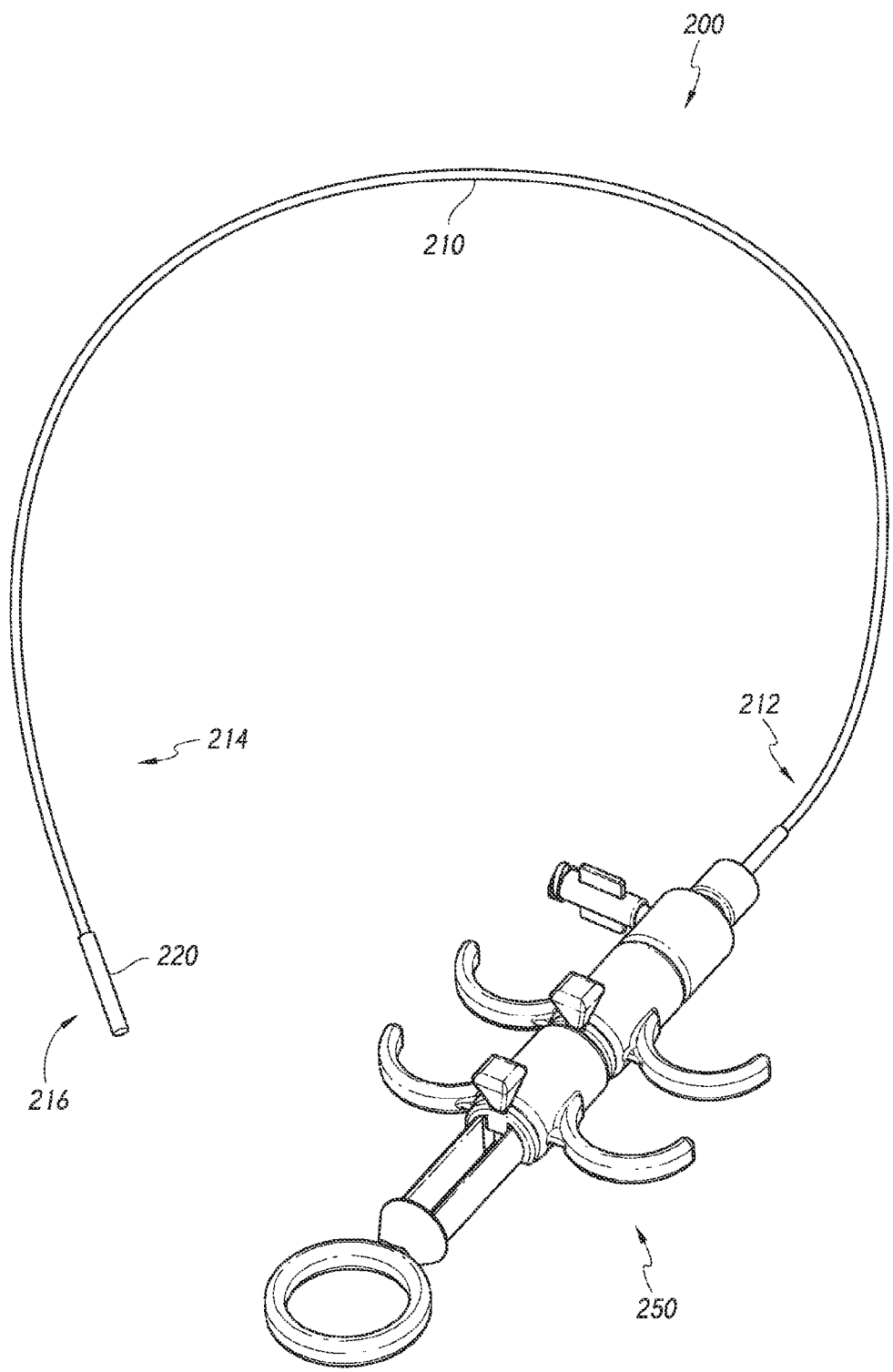
FIG. 3 is a perspective view of an implant carrier assembly, according to some embodiments.

FIG. 3 illustrates an embodiment of an implant carrier assembly 200 can comprise a catheter 210 having a lumen that extends between a proximal portion 212 and a distal portion 214 of the catheter. The catheter 210 can also comprise an engagement section 216, which can be located along a distal portion of the catheter 210, configured to engage and/or restrain an implant positioned therealong. The catheter 210 can define a length from about 50 cm to about 200 cm, from about 70 cm to about 160 cm, or in some embodiments, about 120 cm, with a working length of from about 85 cm to about 140 cm, from about 95 cm to about 130 cm. In accordance with some embodiments, the total length of the implant carrier assembly (with handle) can be about 117 cm, with a working length of 97 cm.

The assembly 200 can also comprise an implant 220 loaded on the engagement section 216. Further, the assembly 200 can also comprise a deployment handle assembly 250 attached to the catheter proximal portion 212.

As noted above, the catheter 210 can be configured to within the guide sheath 102. The proximal portion 212 of the catheter 210 can be configured to be relatively stiff in order to enhance the pushability of the catheter 210 through the guide sheath 102. Further, the distal portion 214 can be relatively flexible in order to improve the maneuverability and trackability of the catheter 210 as it is advanced through the guide sheath 102.

Figure 4:
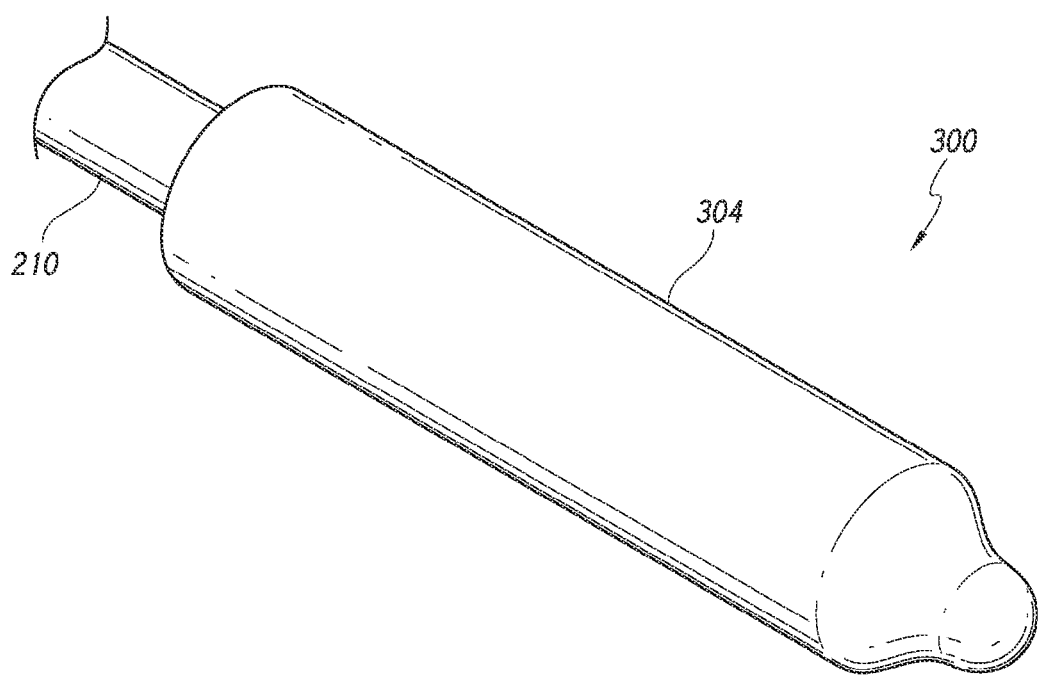
FIG. 4 is a perspective view of an implant in a collapsed state on a carrier assembly, according to some embodiments.
Figure 5A:
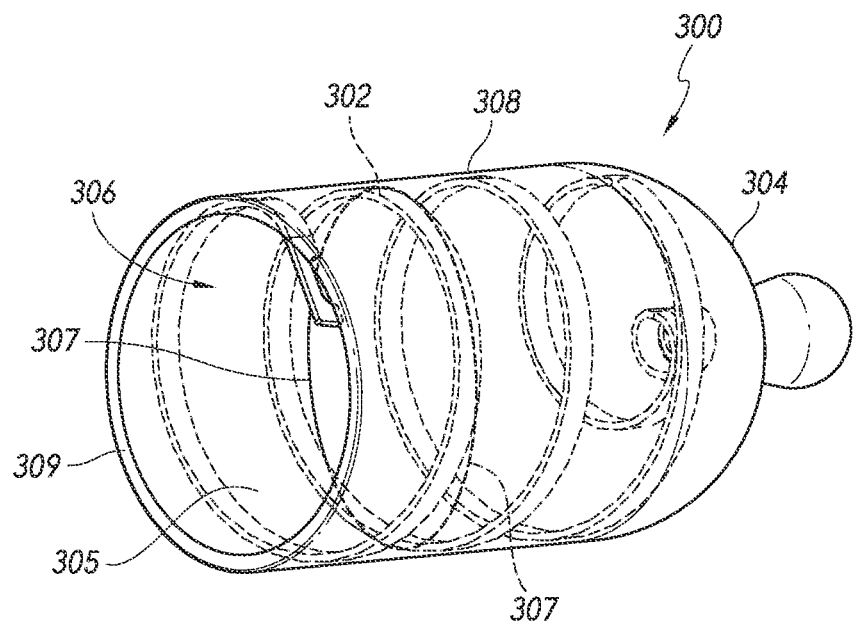
FIGS. 5A-5B are perspective views of implants in an expanded state, according to some embodiments.
Figure 6A:
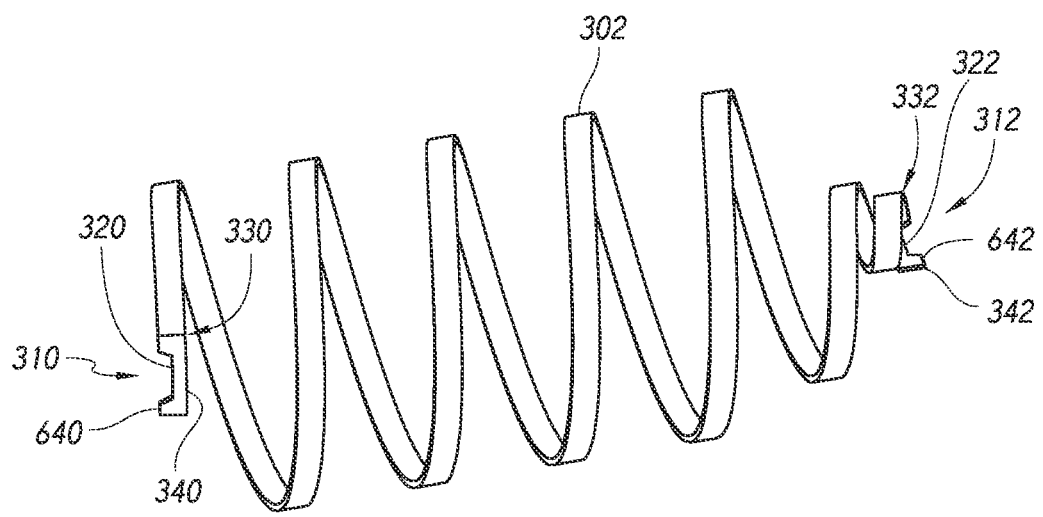
FIGS. 6A-6B are perspective views of support members of implants in an expanded state, according to some embodiments.
Figure 5B:
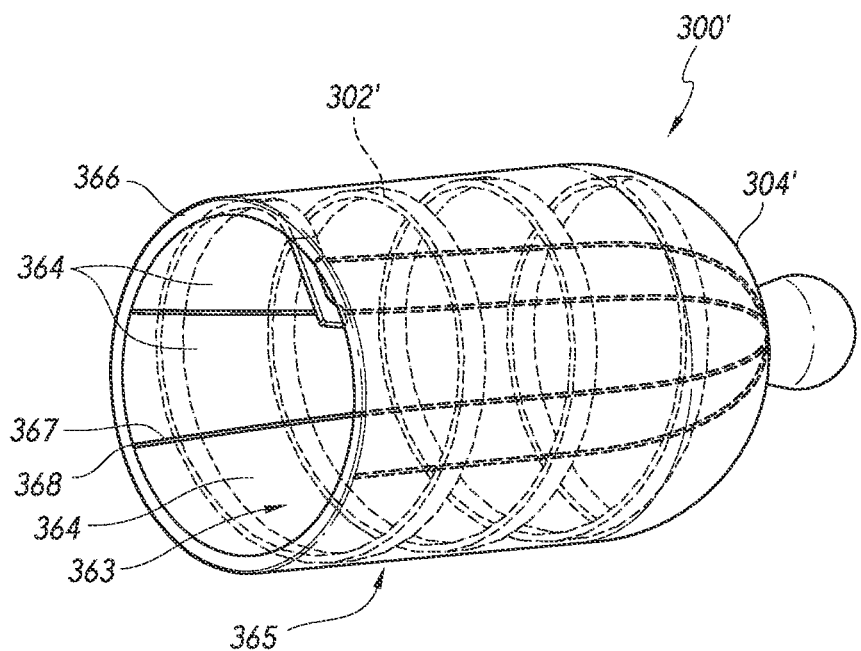
Figure 6B:
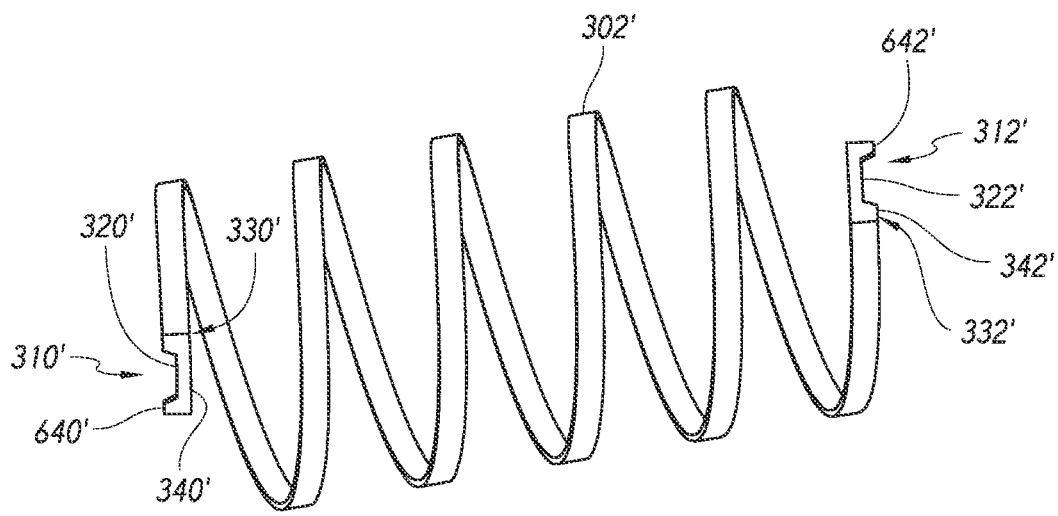

Referring now to FIGS. 4-6B, features of embodiments of implant 300, 300' are illustrated. As shown in FIG. 4, the implant 300 (or 300') can be supported on a distal end of the catheter 210. FIGS. 5A and 6A illustrate that the implant 300 can comprise a helical member, support member, scaffold, or wire 302 and a membrane or cover member 304 supported by the support member 302. Similarly, FIGS. 5B and 6B illustrate that the implant 300' can comprise a support member 302' and a cover member 304' supported by the support member 302'. The support member 302 in the embodiment of FIGS. 5A and 6A has, in its expanded configuration, a tapering distal end. The support member 302' in the embodiment of FIGS. 5B and 6B has, in its expanded configuration, a generally uniform diameter along the entire axial length of the support member 302' (i.e., it does not include a tapered end, including both the proximal and distal ends of the support member 302'. In practice, a generally uniform diameter (as shown in the embodiment of FIGS. 5B and 6B) can advantageously allow the proximal and distal ends of the support member to more completely and predictably expand and disengage from the catheter when released.

The support member 302, 302' can be formed from a variety of materials, which can be flexible or deformable. For example, the support member 302, 302' can comprise nitinol. Additionally, the cover member 304, 304' can comprise one or more of a variety of materials that can be impermeable or have low permeability. In some embodiments, the cover member 304, 304' can be configured to occlude blood flow. For example, the cover member 304, 304' can comprise polytetrafluoroethylene (PTFE), and similar materials, such as expanded polytetrafluoroethylene (ePTFE).

The cover member of the implant can extend at least partially around or about the support member. The cover member can comprise a tubular member having a lumen in which the support member is positioned. Further, the cover member can have a first portion and a second portion. The first portion can radially overlap with the second portion. For example, the first portion can extend within an inner portion or lumen of the support member, and the second portion can extend along an outer portion or exterior of the support member.

The cover member first end portion can also comprise at least one extension member. The extension member can be flexible. The extension member can have a substantially rectangular shape. Further, the extension member can have a width that is greater than its length. Furthermore, the extension member can take the form of an elongate member such as a ribbon, wire, or strip of material. For example, an extension member of the first end portion can be coupled to an uninterrupted, tubular second end portion. Further, the cover member can be configured as a tube having one or more longitudinal slits that separate portions of the tube into one or more extension members.

For example, the first end portion can comprise one or more extension members having free, separate ends. The cover member can comprise at least two, four, or eight extension members. For example, in some embodiments, the cover member can comprise two, three, four, five, six, seven, eight, or more extension members. The cover member can further comprise a transition section at which the first end portion transitions to the second end portion. The transition section can be disposed inside a lumen of the implant or outside the lumen, along an exterior of the implant.

As shown in FIG. 5A, the cover member 304 can be configured as a generally tubular member having a first end portion 305 that folds inwardly into or resides within a lumen 306 of the implant 300. The first end portion 305 comprises a single, undivided portion of material having a free end 307 that resides within the lumen 306. The first end portion 305 is coupled to or extends from a second portion 308 of the cover member 304. In some embodiments, the first end portion 305 is coupled to and can transition into the second end portion 308 along a transition section 309 of the cover member 304. The transition section 309 can be positioned at a proximal edge or end of the implant 300. In some embodiments, the cover member 304 forms a fold at the transition section 309 when the cover member 304 is positioned about or coupled to the support member 302.

Another embodiment of the cover member is illustrated in FIG. 5B. As shown, cover member 304' can comprise a first end portion section 363 having a plurality of extension members 364. The extension members 364 can extend from a second section 365. According to some embodiments, the first and second sections 363, 365 can meet at a transition section 366, which can be positioned adjacent to a proximal edge or end of the implant 300'. In some embodiments, the cover member 304' forms a fold at the transition section 366 when the cover member 304' is positioned about or coupled to the support member 302'.

The extension members 364 can be separated by respective slits 367. Each slit 367 can have an origin end 368 at the transition section 366 of the first and second sections 363, 365, and a terminal end (not shown) at the distal end portion of the first section 363. According to some embodiments, the cover member 304' can be positioned on the support member 302' such that the transition section 366 (or the origin end 368 of each slit 367) is positioned along or abuts the fold formed in the cover member 304'. However, the transition section 366 (or the origin end 368) can also be positioned inside or outside the lumen, along an exterior of the support member 302'. For example, the origin end 368 of the slit 367 can be spaced apart from the fold 366 at a distance less than three quarters, less than two thirds, less than one half, less than one third, or less than one fourth of an axial length of the expanded support member, and either disposed within the lumen or outside of the lumen, along an exterior surface of the implant.

Some embodiments can be configured such that the slits and extension members are formed by cutting the cover member without removing any substantial amount of material between the extension members. For example, the slit can be formed such that it has substantially no width. Such embodiments can be created, for example by a mechanical blade, a laser, or other means.

However, some embodiments can be provided in which the extension members are separated by slits formed by removing material from the cover member. For example, a slit can be formed by cutting out material to create a substantial width to the slit, for example, greater than 0.4 mm, greater than 0.8 mm in width, greater than 1 mm in width, greater than 2 mm in width, or greater than 3 mm in width. The size of the slit width can be between about 1/20 to about 8 times the size of a corresponding extension member formed in the cover member first end portion.

According to some embodiments, the use of a plurality of extension members 364 can allow the implant to be assembled and delivered through a much lower profile catheter than previously performed. For example, the applicant has unexpectedly found that the use of a plurality of extension members 364 has allowed such embodiments of the implant to be inserted into a catheter having a size of less than 6 Fr, such as between about 5.0 Fr and about 5.9 Fr, such as 5.0 Fr, 5.1 Fr, 5.2 Fr, 5.3 Fr, 5.4 Fr, 5.5 Fr, 5.6 Fr, 5.7 Fr, 5.8 Fr, or 5.9 Fr. By contrast, corresponding implants differing only in that they do not use a plurality of extension members 364 can only be inserted into a catheter having a minimum size of 6.8 Fr. Thus, some embodiments can advantageously provide further reductions in size based on the configuration of the first end portion of the implant.

When implanted into a vessel, the implant 300, 300' can be configured to provide sufficient radial strength against a vessel wall under normal blood pressure in order to minimize post-deployment migration.

The implant 300, 300' can be configured with an expanded diameter depending on the target vessel size. For example, the implant 300 can have an expanded diameter of about 6 mm for vessels from about 3.0 mm to about 4.8 mm in diameter. Further, the implant can have an expanded diameter of about 9 mm for vessels from about 4.5 mm to about 7.8 mm in diameter. Additionally, such embodiments can be compatible with, for example, a guide catheter with a size of between 5 Fr and 8 Fr.

Referring now to FIG. 6A, in some embodiments, the implant support member 302 can be formed as a helical body. For example, the support member 302 can define proximal and distal sections 310, 312. The body can be braided or comprise a single helical member. Generally, the body of the support member 302 can extend along a curvilinear, helical path. However, in accordance with some embodiments, one or both of the proximal or distal sections 310, 312 can bend radially inwardly from the helical path. In some embodiments, one or both of the proximal or distal sections 310, 312 can be configured to extend across the lumen of the support member 302, and/or across the lumen of the catheter 210, as discussed further below.

For example, the proximal section 310 can be configured to include an elbow 330 that causes a portion of the proximal section 310 to diverge from the generally helical path of the support member 302. The elbow 330 can comprise a change to a smaller radius of curvature compared to the radius of curvature of the helical path. Further, in some embodiments, the elbow 330 can define a generally right angle orientation for the proximal section 310.

Additionally, in some embodiments, the distal section 312 can also comprise an elbow 332. The elbow 332 can be configured similarly to the elbow 330 and allow a divergence in the path of the support member 302 at the distal section 312 thereof.

Further, in some embodiments, one or both of the proximal or distal sections 310, 312 can comprise a generally planar portion. For example, the proximal section 310 can comprise a planar portion 340 that extends from the elbow 330. The planar portion 340 can comprise a portion of the proximal section 310 that diverges from the helical path and extends generally within a plane. Thus, the planar portion 340 can be referred to as a flat or flattened portion that can extend in a generally linear or curvilinear direction within a plane. In some embodiments, the distal section 312 can also comprise a planar portion, which is illustrated in FIG. 6A as planar portion 342.

The planar portions 340, 342, whether either or both of them are included in an embodiment, can extend or bend radially inwardly from the helical path of the support member 302. Similarly, one or both of the planar portions 340, 342 can be configured to extend across the lumen of the support member 302, and/or across the lumen of the catheter 210, as discussed further below.

The support member 302 can comprise one or more reduced cross-sectional segments, notches, cut-outs, or indentations 320, 322. The segments 320, 322 can be disposed at the proximal section 310 and/or the distal section 312 of the support member 302. For example, FIG. 6A illustrates that the proximal section 310 comprises the reduced cross-sectional segment 320 and the proximal section 312 comprises a reduced cross-sectional segment 322.

In the illustrated embodiment, the reduced cross-sectional segments 320, 322 can comprise notches in the body of the support member 302. For example, the support member 302 can comprise a generally rectangular cross section and extend helically about a central axis or lumen, as illustrated in FIG. 6A. The reduced cross-sectional segments 320, 322 can be indentations, protrusions, slots, and/or apertures extending through the support member 302. As discussed further below, the segments 320, 322 can be configured to interact with respective structures of the engagement section 216 of the catheter 210.

Figure 7B:
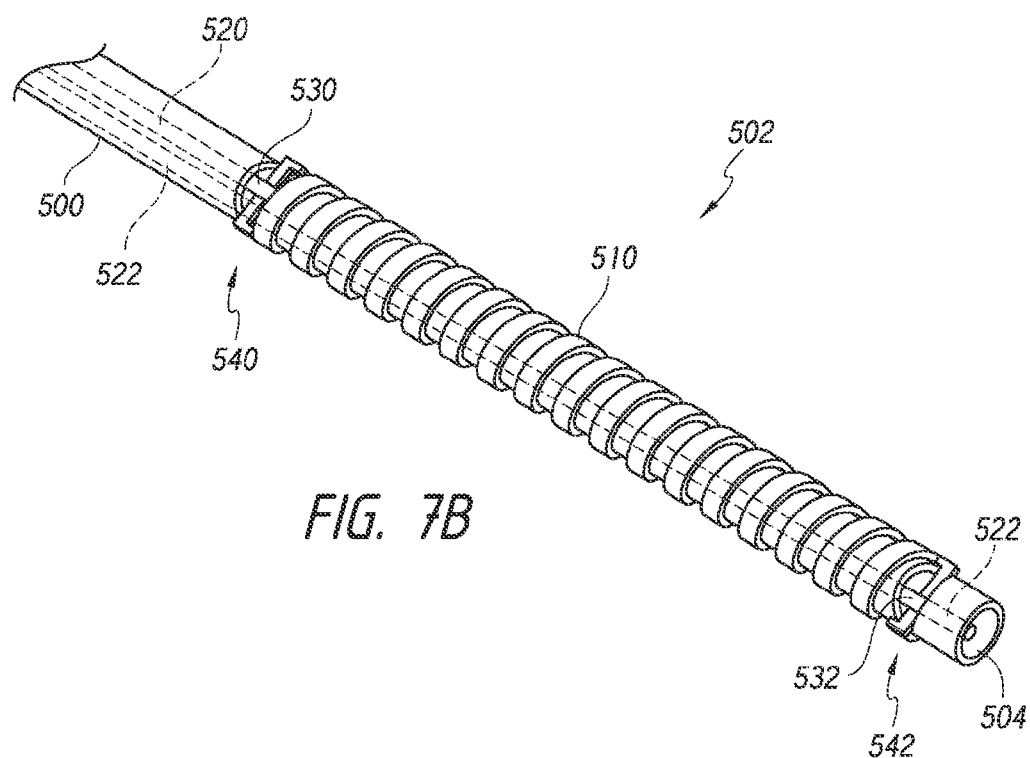

For example, FIGS. 7A-7E illustrate some embodiments of implant carrier assemblies. FIG. 7A illustrates an enlarged view of an engagement section or seat 216 located at a distal portion 214 of the catheter 210. The catheter 210 can comprise a lumen 400 extending through the catheter 210 and a catheter wall 402 formed between the catheter lumen 400 and an exterior surface 404 of the catheter 210.

FIG. 6B illustrates another embodiment of a support member, which can include the various features discussed above with regard to the support member 302. As illustrated, the support member 302' can comprise proximal and distal sections 310', 312', reduced cross-sectional segments 320', 322', elbows 330', 332', planar portions 340', 342', and tabs 640', 642'. These features of the support member 302' can be implemented as discussed above with respect to such features of the support member 302, and therefore, the discussion of such features is incorporated herein by reference and will not be repeated.

As shown in FIG. 7A, the engagement section 216 can be configured to receive and facilitate engagement with at least a portion of an implant (illustrated only as support member 302, but which can include a cover member, as discussed above) to maintain the implant engaged with the distal end 214 of the catheter 210.

In accordance with some embodiments, the implant carrier assembly 200 can also be configured to comprise at least one elongate member 420 that extends at least partially through the catheter lumen 400. The elongate member 420 can engage at least a portion of, and in some embodiments, one or both the proximal and distal sections 310, 312, of the support member 302. The elongate member 420 can comprise a wire. However, in some embodiments, the elongate member 420 can comprise a plug or other structure that can interact with one or both of the proximal or distal sections 310, 312 of the implant 300.

In some embodiments, the elongate member 420 can be actuatable or controllable using the handle assembly 250, as discussed further below.

For example, the engagement section 216 can be configured to facilitate engagement between the support member 302 and the elongate member 420 extending from the handle assembly. In some embodiments, the elongate member 420 can be selectively actuated or withdrawn in order to release engagement between the support member 302 and the elongate member 420. The movement of the elongate member 420 can be configured to be a proximal withdrawal of the elongate member 420. However, the elongate member 420 can also be configured such that disengagement occurs when the elongate member is distally advanced (such as when a proximally oriented hook or segment of the elongate member 420 engages with the support member 302). Indeed, the elongate member 420 can be moved a first distance (whether proximally or distally) in order to release or disengage with one of the proximal or distal sections 310, 312 of the support member 302. Further, the elongate member can be moved a second distance, greater than the first distance (whether proximally or distally) in order to release or disengage with the other one of the proximal or distal sections 310, 312 of the support member 302.

Further, in some embodiments, the engagement section 216 can facilitate engagement between the implant 300 and two or more elongate members 420 extending from the handle assembly 250. Although the elongate member 420 is illustrated as extending between the proximal and distal sections 310, 312 of the implant support member 302, the elongate member 420 can engage one of the proximal or distal sections 310, 312 while a second elongate member can be used to engage the other of the proximal or distal sections 310, 312.

For example, FIG. 7B illustrates an embodiment of an implant assembly in which a catheter 500 comprises an engagement section 502 and a lumen 504. The assembly can comprise an implant or support member 510 supported on the engagement section 502. Further, the assembly can comprise a first elongate member 520 and a second elongate member 522 configured to engage with the support member 510. As shown, a distal portion 530 of the elongate member 520 can engage a proximal portion 540 of support member 510 and a distal portion 532 of the elongate member 522 can engage with a distal portion 542 of the support member 510.

Accordingly, in embodiments that comprise two elongate members, the elongate members can be actuated independently of each other in order to control the release of the respective proximal or distal sections 310, 312 of the support member 302 or implant 300.

Referring again to FIG. 7A, the catheter 210 can be configured to comprise an engagement section having at least one engagement component, which can comprise a notch, slot, aperture, opening, or indentation in the catheter 210. For example, the catheter 210 illustrated in FIG. 7A comprises a proximal aperture 600 and a distal aperture 602. The proximal and distal aperture 600, 602 are configured to extend through the wall 402 of the catheter 210. Further, the apertures 600, 602 are configured as slots or notches that extend transversely relative to a longitudinal axis of the catheter lumen 400. The apertures 600, 602 can extend radially at least partially into the lumen 400, and as illustrated, can extend about halfway across a diameter of the lumen 400. In some embodiments, the aperture 600, 602 can extend radially through from about ¼ to about ¾ of the diameter of the lumen 400, through from about ⅓ to about ⅔ of the diameter of the lumen 400, or in some embodiments, through about ½ of the diameter of the lumen 400.

For example, as illustrated in FIG. 7B, some embodiments can be configured such that at least one of the proximal or distal sections 310, 312 of the support member 302 extends within the respective proximal or distal aperture 600, 602 of the catheter 210.

Further, FIG. 7B also illustrates the support member 302 of the implant 300 in a mounted, collapsed, or wound position. In the mounted, collapsed, or wound position, the support member 302 can be wound around the engagement section or catheter distal portion with about 10 to about 25 winds, from about 15 to about 20 winds, or in some embodiments about 16 or about 19 winds. Thus, before the support member 302 or stent 300 is released, the support member 302 is helically wound tightly around the catheter 210. The winding of the support member 302 about the engagement section or catheter distal portion can put the support member 302 into a stressed state. As discussed further below, the support member 302 will tend to rebound or expand from the stressed, mounted, collapsed, or wound position.

Additionally, some embodiments can be configured such that an elongate member extends through the catheter lumen and between at least one of the proximal or distal sections of the support member and the wall of the catheter. For example, the elongate member can be disposed radially between the proximal or distal section of the support member and the wall of the catheter.

For example, FIG. 7C illustrates the configuration of the catheter 302 and the aperture 600 in relation to the elongate member 420 and the proximal section 310 of the support member 302. As shown, the proximal section 310 can sit within the aperture 600 and provide enough clearance between the proximal section 310 and wall 402 or the inner surface of the wall 402 such that the elongate member 420 can be positioned intermediate the wall 402 and the proximal section 310. As also shown, the proximal section 310 can extend across the entire diameter of the lumen 400 and a transverse direction. However, the proximal and/or distal sections 310, 312 can also be configured to extend across the lumen 400 less than a diameter of the lumen 400 (whether in the transverse direction or in a radial direction).

Accordingly, the elongate member 420 can secure the proximal section 310 within the aperture 600 to prevent movement of the proximal section in an axial direction 646 (shown in FIG. 7A) and/or a radial direction 648 (shown in FIG. 7C). In some embodiments, the support member 302 can be a resilient or self-expanding support member, such that the proximal section 310 will tend to expand or move out of the aperture 600 without the presence of the elongate member 420. Thus, when the elongate member 420 is in place between the proximal section 310 and the wall 402 of the catheter 210, the proximal section 310 can be retained or engaged within the aperture 600.

The engagement illustrated in FIG. 7C between the proximal section 310, the elongate member 420, and the aperture 600 can also be present at the distal end of the support member 302, although it will not be discussed further herein. However, as noted, some embodiments can be implemented in which a single end of the support member is retained within an aperture or otherwise engaged by the elongate member.

Additionally, FIGS. 7A and 7C illustrate that the reduced cross-sectional segments 320, 322 can be positioned within the respective apertures 600, 602. For example, the reduced cross-sectional segments 320, 322 and the respective apertures 600, 602 can each have substantially equal lengths, measured in the direction transverse to an axis of the lumen 400. Thus, a given reduced cross-sectional segment can be seated or received into a respective aperture and achieve a fit with the aperture such that the respective proximal or distal section of the support member is generally restrained against movement or rotation in a direction 650 transverse to an axis of the lumen 400.

For example in some embodiments, the proximal and/or distal sections 310, 312 can comprise planar portions, as illustrated in discussed above with respect to FIG. 6A and 6B. Additionally, as also shown in FIG. 6A, the proximal and/or distal sections 310 can comprise an end or tab 640, 642 extending therefrom. The tabs 640, 642 can be disposed at the distal ends of the proximal and distal sections 310, 312. The tabs 640, 642 can also be larger than the section of the proximal or distal section 310, 312 extending through the aperture 600, 602 (which can be the reduced cross-sectional segments 320, 322, in some embodiments).

For example, the tabs 640, 642 can be a portion of the proximal and distal sections 310, 312 that extends from, remains, or is disposed adjacent to ends of the reduced cross-sectional segments 320, 322. The tabs 640, 642 can protrude from and create an interference against the outer surface of the catheter 210 in order to block or inhibit motion of the respective proximal or distal section 310, 312. For example, the tabs 640, 642 can be configured to extend out of the apertures 600, 602 and to abut an outer surface of the catheter 210, thereby generally restricting movement or rotation of the respective proximal or distal section of the support member in a direction 650 transverse to an axis of the lumen 400. The width or length of the reduced cross-sectional segments 320, 322 can be bound on one end by the respective tab 640, 642 and on the other end by the non-reduced or original cross-sectional segment of the support member 302 adjacent the reduced cross-sectional segments 320, 322. The width or length of the reduced cross-sectional segments 320, 322 can be configured such that the proximal and/or distal section 310, 312 can be seated within the respective engagement section or aperture 600, 602 such that the proximal and/or distal section 310, 312 is restrained from movement transverse to an axis of the catheter 210 when the elongate member 420 is engaged with and radially restraining the proximal and/or distal section 310, 312 within the respective engagement section or aperture 600, 602. For example, in some embodiments, the reduced cross-sectional segments 320, 322 and the apertures 600, 602 can each have substantially equal lengths or widths, transverse to an axis of the catheter 210, and be configured to engage each other.

Accordingly, some embodiments can be configured such that the proximal and/or distal sections 310, 312 can be constrained against movement in an axial direction 646, a radial direction 648, and a transverse direction 650. Thus, when the implant 300 or support member 302 is coiled about the engagement section 216 of the catheter 210, the proximal and distal sections 310, 312 of the support member 302 can be secured in various directions to be engaged during delivery of the implant 300 to the treatment site. When the implant 300 reaches the treatment site, the implant 300 can then be expanded.

Figure 7D:
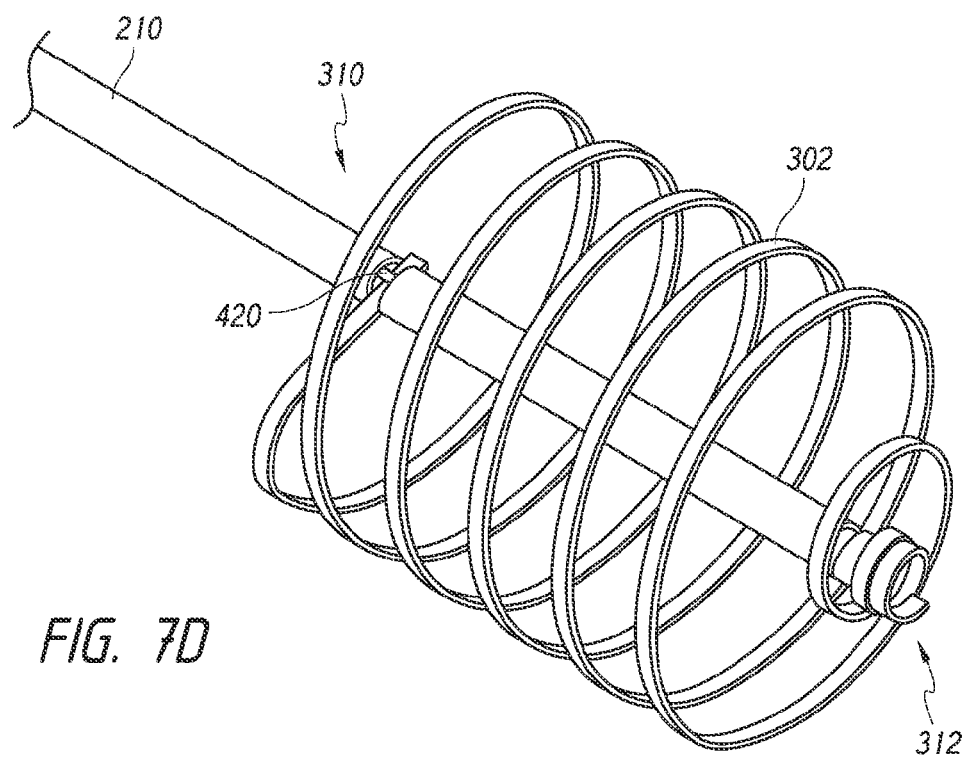

An initial phase of the implant expansion is illustrated in FIG. 7D. As shown, the proximal portion 310 of the support member 302 is engaged or retained by an elongate member 420. However, the support member 302 has expanded from a mounted or collapsed state (shown in FIG. 7B) to an expanded state (shown in FIG. 7D) because the distal section 312 of the support member 302 has been released from engagement with the catheter 210. When released, the stress in the wound support member 302 can be released as the implant distal section 312 unwinds (perhaps along with a portion of the support member 302 intermediate the proximal and distal sections 310, 312). For example, the distal and proximal sections 310, 312 can rotate or unwind relative to each other, allowing the diameter of the implant 300 to expand while it unwinds or rotates. The support member 302 can have fewer winds in the expanded position when the support member 302 has achieved a target diameter (likely configured to be slightly larger than the interior dimensions of the target vessel to allow the implant 300 to be urged into contact with the vessel wall). For example, in the expanded, unwound position, the support member 302 can have from about 4 to about 10 winds, from about 5 to about 8 winds, and in some embodiment about 6 or about 7 winds.

Thereafter, in order to fully release the support member 302, the engagement member 420 can be moved (either proximally or distally, depending on the configuration of the engagement member 420) in order to disengage from the proximal section 310 of the support member 302.

Figure 7E:
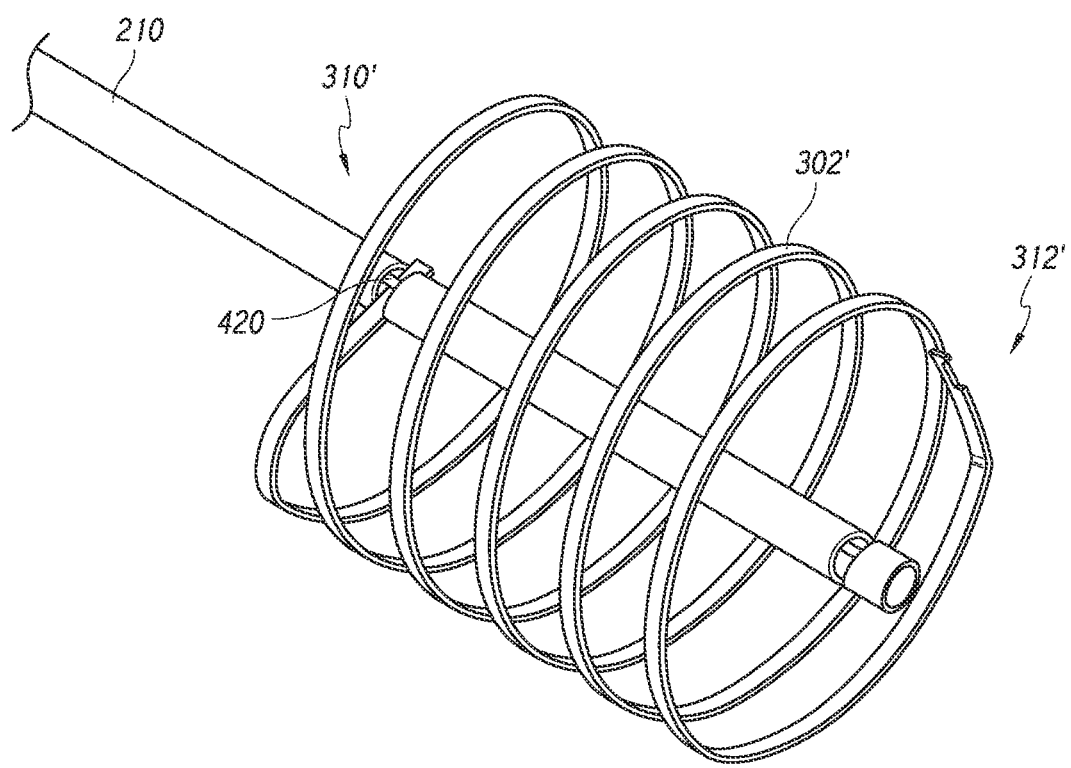

FIG. 7E illustrates another embodiment in which support member 302' has been partially released from the catheter 210. The support member 302', which is shown and described above in FIG. 6B, is expanded to a generally cylindrical configuration in FIG. 7E by releasing or disengaging the distal section 312' from the catheter 210. According to some embodiments, such as that illustrated in FIGS. 6B and 7E, when released and expanded to the expanded configuration, the support member proximal and distal sections 310', 312' can tend to follow along the helical path of the support member 302', even if the elbows 330', 332' are included.

The support member 302' can advantageously provide excellent releasing characteristics. For example, the proximal and distal sections 310', 312' can be configured to extend along a generally tubular, helical path (i.e., not be tapered). Thus, when the proximal and distal sections 310', 312' are released, they can quickly separate from the catheter 210 to become spaced apart from and fully disengaged from the catheter 210, as illustrated in FIG. 7E. Accordingly, any interference between the proximal or distal sections 310', 312' and the catheter 210 will be minimized or eliminated.

Further, in some embodiments, when expanded, the support member 302' can fit within the cover member and be capable of rotating within the cover member without catching, snagging, or otherwise engaging the cover member to cause the cover member to rotate, twist, or otherwise be pulled when the support member is expanding. Such embodiments can be configured such that the entire support member follows along the helical path to form a tubular member. The cover member can at least partially surround or envelope, along the interior and/or exterior of the support member, without being fixed relative to the support member. For example, when the support member expands from the collapsed configuration, the support member can unwind (which causes one or both ends of the support member to move around the circumference of the implant). If one or both of the unwinding, moving ends of the support member are coupled to the cover member, the cover member may tend to move or twist in response to the movement of the support member ends. However, in some embodiments, the support member can be at least partially surrounded or enveloped by the cover member and be freely movable within the cover member, such that movement of the support member during expansion does not exert a torsional or twisting force on the cover member. Thus, the support member can cause the cover member to radially expand without causing the cover member to twist.

Figure 8:
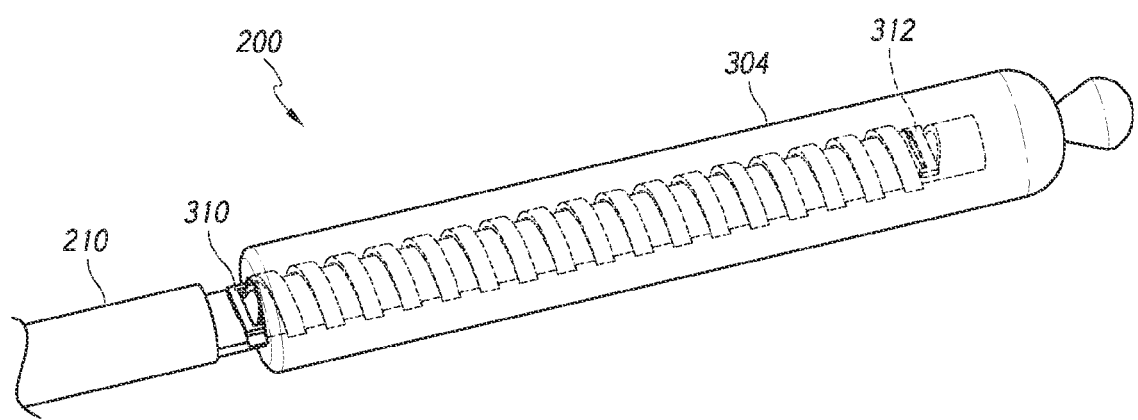
FIG. 8 illustrates a perspective view of an implant in a mounted or collapsed position on a catheter, according to some embodiments.

FIG. 8 illustrates a perspective view of the implant carrier assembly 200, similar to the illustrations of FIGS. 7A-7B, but further including the implant cover member 304. As illustrated, the implant cover member can be positioned over the support member 302 and delivered in a mounted or collapsed state. The elongate member 420 can be engaged with the proximal section 310 of the support member 302. Further, as noted above, the elongate member 420 or a different elongate member can be engaged with the distal section 312 of the support member 302.

FIGS. 9A-10E illustrate features of methods for manufacturing an occlusion device and mounting the occlusion device on an implant carrier assembly, according to some embodiments. In accordance with embodiments disclosed in FIGS. 9A-10E, the implant carrier assembly can include one or more features or structures that facilitate engagement between the catheter of the carrier assembly and an implant supported thereon. Some embodiments of methods or procedures for preparing or loading the implant onto the catheter are discussed and illustrated in FIGS. 9A-10E. As a preliminary step, in assembling the implant carrier assembly, the catheter can be cleaned and prepared prior to assembling the components of the device and carrier assembly. According to some embodiments, the method can be implemented by positioning or securing a support member over an engagement section of a catheter and attaching a cover member to the support member.

Features of embodiments of the implants disclosed herein can also be implemented in methods of manufacturing the occlusive device. For example, the support member can be self-expanding and can be compressed or wound onto the engagement section of the catheter, which can be along a distal portion of the catheter. The support member can be secured to the engagement section by engaging one or both end portions of the support member relative to the catheter distal end. For example, one or both end portions of the support member can be inserted into respective apertures in the engagement section to engage with one or more elongate members or wires. The engagement between the elongate member(s) and the end portion(s) of the support member can enable the device to be maintained in a collapsed configuration on the catheter and subsequently expanded.

For example, FIG. 9A illustrates a catheter 210 having an engagement section 216 along a distal portion 214 thereof. The engagement section 216 can comprise first and second notches, slots, or apertures 600, 602. The first aperture 600 can be positioned proximal to the second aperture 602, along the catheter 210. As shown in FIG. 9A, prior to placing a support member over the catheter 210, a first section 652 of a cover member 653 can be positioned over the first aperture 600. As illustrated in FIG. 9B, a distal end 664 of the cover member 653 can be positioned longitudinally between the first and second apertures 600, 602 of the catheter 210.

Once the first section 652 of the cover member 653 is positioned over the first aperture 600, a support member 654 can be placed over and secured to the catheter 210 to at least partially surround or cover the first section 652 of the cover member 653. As discussed herein, in some embodiments, the support member 654 can be secured relative to the catheter 210 through the use of at least one elongate member 656. Other embodiments discussed above, in which two elongate members are used, can also be implemented in embodiments of the methods discussed herein.

In securing the support member 654 to the catheter 210, a proximal section 658 of the support member 654 is placed into the first aperture 600, thus causing a portion 659 of the first section 652 of the cover member 653 to be pushed or received within the first aperture 600. With the proximal section 658 at a base or bottom of the first aperture 600, the elongate member 656 can be urged into place. The elongate member 656 can be positioned between the proximal section 658 of the support member 654 and the catheter 210. For example, the elongate member 656 can be interposed radially between of the proximal section 658 and a wall 660 of the catheter 210.

Figure 9E:
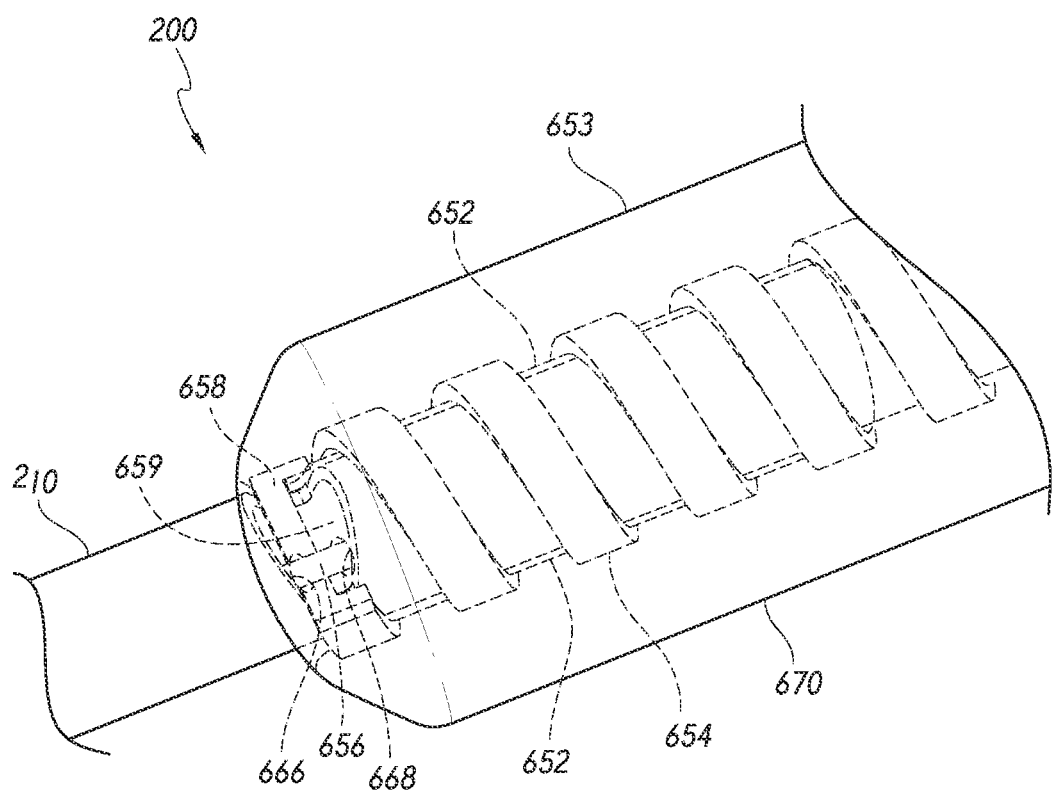

As illustrated in FIGS. 9B and 9E, when the elongate member 656 is urged into engagement with the proximal section 658, the elongate member 656 can pierce the portion 659 of the cover member 653. As the distal tip of the elongate member 656 enters the first aperture 600, the distal tip will pierce the cover member portion 659 in a first location to create a first hole 666 and, as the distal tip of the elongate member 656 exits the first aperture 600, the distal tip will pierce the cover member portion 659 and a second location to create a second hole 668. Thus, in such embodiments, advancing the elongate member 656 into engagement with the proximal section 658 can require piercing of the cover member 653, for example, along the first section 652 of the cover member 653.

In some embodiments, the elongate member 656 (or a second elongate member, not shown) can be advanced into engagement with a distal section 662 of the support member 654. The distal section 662 of the support member 654 can be engaged by being inserted into the second aperture 602 and placing an elongate member into the second aperture 602 between the distal section 662 and the catheter 210. The elongate member can be interposed radially between the distal section 662 and the wall 660 of the catheter 210.

After the support member 654 is engaged and secured to the catheter 210 with the first section 652 of the cover member 653 interposed between the support member 654 and the catheter 210, the cover member 653 can then be everted over the support member 654, as shown in FIG. 9C. A second section 670 of the cover member 653 can be everted such that an end 672 of the second section 670 extends distally beyond a tip 674 of the catheter 210. Once the end 672 of the second section 670 is in place, the end 672 can be closed, using, for example, a suture, clip, adhesive, or other such means, to form a closed end portion 676. When closed, the closed end portion 676 will substantially prevent any fluid from passing beyond the closed end portion 676.

Referring now to FIGS. 10A-10E, the implant carrier assembly and the implant can be assembled by placing or securing the support member onto the distal portion or engagement section of the catheter before positioning the cover member over the engagement section of the catheter. The above discussion of the engagement process and related features of the implant or carrier assembly is incorporated herein by reference and will not be repeated. The support member can be secured relative to the catheter using any of the methods or features discussed herein. Further, the cover member can be placed into engagement with the support member after the support member has been secured to the engagement section of the catheter.

In some embodiments, prior to placing the support member over the engagement section of the catheter, one or more pulling members or wires can be placed over the engagement section of the catheter. Thereafter, the support member can be positioned or secured to the engagement section of the catheter. When placing the support member, care can be taken to ensure that the pulling member is not pushed into one of the first or second apertures of the catheter, thus allowing the pulling member to maintain a generally straight, elongate configuration, slidable between turns of the support member and the outer surface of the catheter. According to some embodiments, a pulling member can be used to engage and pull one or more extension members of the cover member. For example, if the cover member has eight extension members, two or four pulling members can be used, with each pulling member engaging multiple extension members. Further, according to some embodiments, a pulling member can comprise a wire having a size of about 0.004 inches to about 0.006 inches.

FIG. 10A illustrates a support member 680 placed or secured to the catheter 210 and a pulling member 686 positioned therebetween. However, in some embodiments, the wire can be inserted between the support member and the catheter and advanced in a proximal direction from a distal end portion of the support member after the support member is secured to the catheter.

As shown in FIG. 10B, a first section 681 of a cover member 682 can be placed into engagement with the support member 680. For example, the first section 681 can be drawn into a lumen of the support member 680. Further, the first section 681 can comprise a plurality of extension members 685. In some embodiments, one or more ends 684 of the extension members 685 can be engaged and pulled in a distal direction such that the first section 681 becomes interposed between the support member 680 and the catheter 210. For example, the extension member ends 684 can be drawn between the support member 680 and an outer surface of the catheter 210. The extension member end(s) 684 can be engaged by a pulling member 686. The pulling member 686 can use a hook that pierces the extension member end(s) 684, a loop through which the end(s) 684 is inserted, or an adhesive between the pulling member 686 and the extension member end(s) 684.

FIGS. 10B-10C illustrate the distal pulling or advancement of the ends 684 of the extension members 685 of the cover member 682. The extension member ends 684 can be distally pulled to a position beyond a distal end 688 of the catheter 210 (FIG. 10C). Thereafter, a second section 690 of the cover member 682 can be everted over the support member 680. An end 692 of the cover member second section 690 can be distally everted to a position beyond the distal end 688 of the catheter 210, as also shown in FIG. 10C. Thus, in such an embodiment, the cover member 682 is not drawn into or received within the first or second apertures 600, 602 of the catheter 210. After the ends 684 (and perhaps, ends 692) of the cover member 682 are drawn into position, the pulling member(s) 686 can be disengaged from the extension member ends 684.

As illustrated in FIG. 10D, once the ends 684, 692 are positioned beyond the distal end 688 of the catheter 210, the ends 684, 692 can be coupled together, using, for example, a suture, clip, adhesive, or other such means, to form a closed end portion 694. When closed, the closed end portion 694 will substantially prevent any fluid from passing beyond the closed end portion 694. Further, according to some embodiments, the cover member 682 generally envelops the inner and outer portions of the support member 680. Further, with the ends 684, 692 of the cover member 682 secured to each other, the cover member 682 will tend to remain attached or coupled to the support member 680 by virtue of the enveloping configuration of the cover member 682. Thus, the cover member 682 will not tend to drift or become separated from the support member 680 during use. Furthermore, because such an embodiment does not require a suture, adhesive, or any other type of attachment between the support member 680 and the cover member 682, the cover member 682 will not tend to twist or deform during expansion of the support member 680.

Figure 10E:
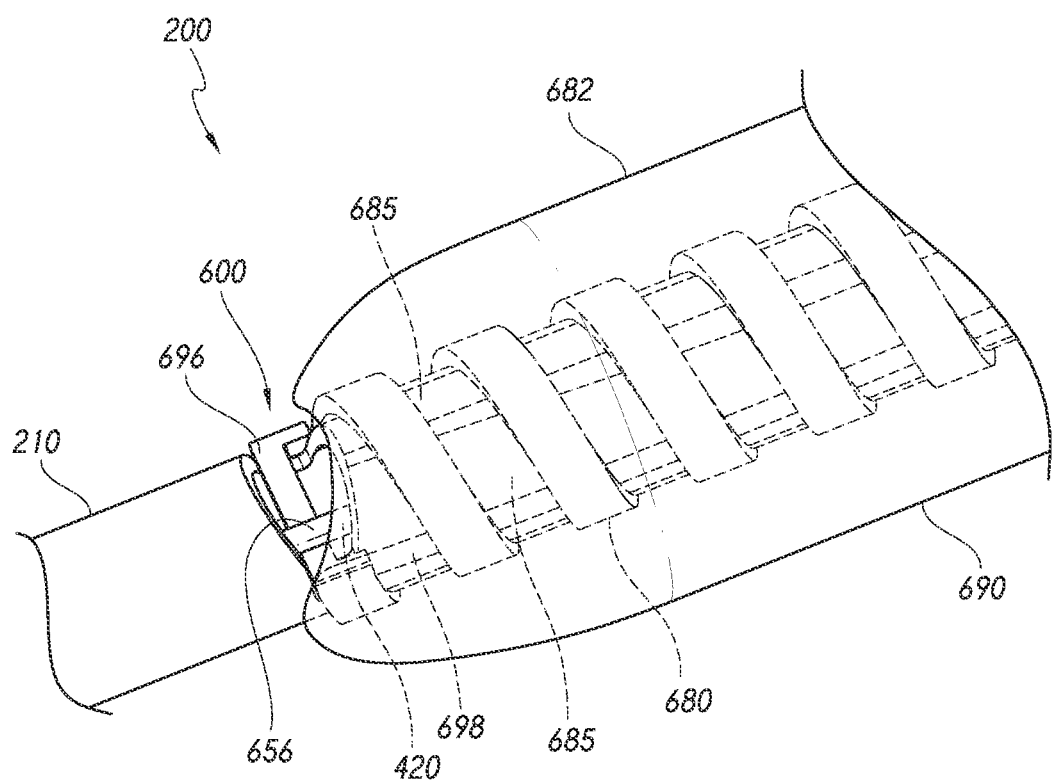

FIG. 10E illustrates a perspective end view of an embodiment of a proximal end of the implant after the cover member 682 has been everted over the support member 680. According to some embodiments, when the second section 690 is everted over the support member 680, a proximal section 696 of the support member 680 can pass through a slit 698 formed between adjacent extension members 685 of the cover member 682. Thus, the proximal section 696 of the support member 680 can be engaged by the elongate member 656 in the aperture 600 of the catheter 210. However, the proximal section 696 will not tend to be engaged with or otherwise secured relative to the cover member 682. Thus, when the support member 680 is released from engagement with the catheter 210, the proximal section 696 can exit the slit 698 and move relative to the cover member 682 without being engaged with the cover member 682 such that the proximal section 696 does not exert a torsional or twisting force on the cover member 682. Accordingly, the support member 680 can move generally independently of the cover member 682, causing the cover member 682 to expand radially without exerting a torsional force on the cover member 682.

Additionally, in some embodiments of the methods disclosed herein, a cover member having an extension member along the first section thereof can placed onto the catheter prior to placement or securement of the support member onto the catheter.

As noted above with respect to some embodiments, the use of a cover member having a plurality of extension members can tend to allow the carrier assembly to have a lower cross-sectional profile or size such that carrier assemblies so configured can be used in catheters of a smaller size than carrier assemblies that do not use a cover member having a plurality of extension members.

Figure 11:
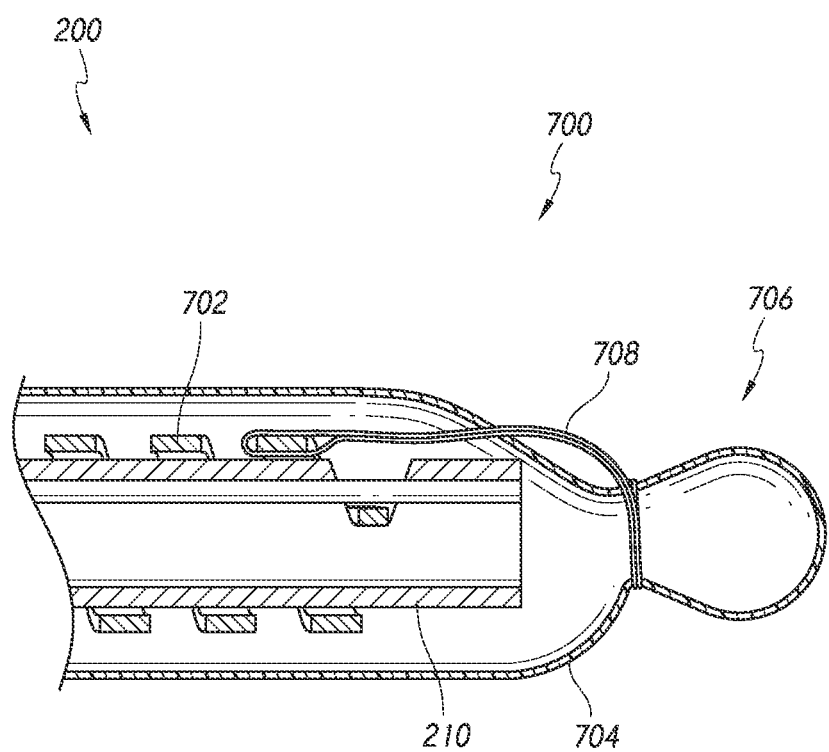
FIGS. 11 is a cross-sectional perspective view of a closed end of an implant, according to some embodiments.

FIG. 11 illustrates an embodiment of an implant distal end 700 in which, in its assembled state, the distal end 700 is sutured or otherwise attached to a support member 702 of the implant. For example, after a cover member 704 of the implant is everted and a closed end portion 706 is formed, a suture 708 can be passed through the cover member 704 and it engaged with one or more turns of the support member 702.

Figure 12:
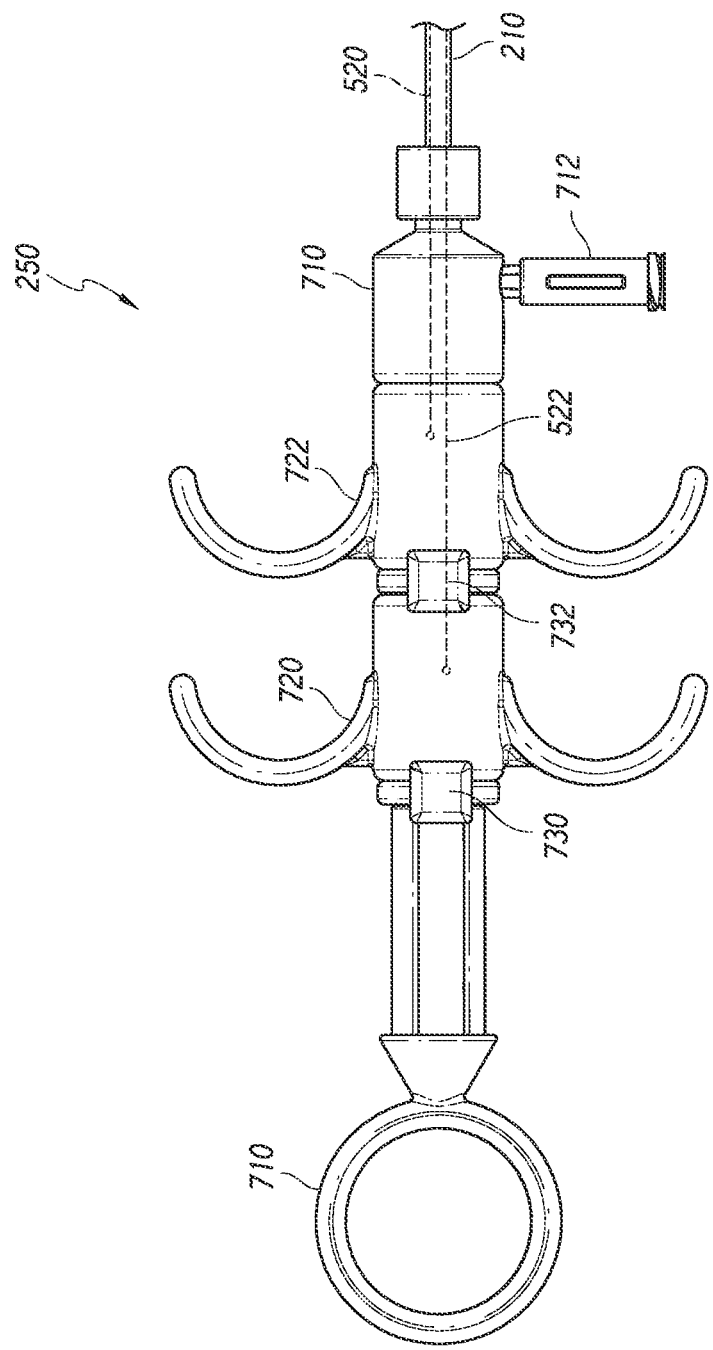
Figure 15A:
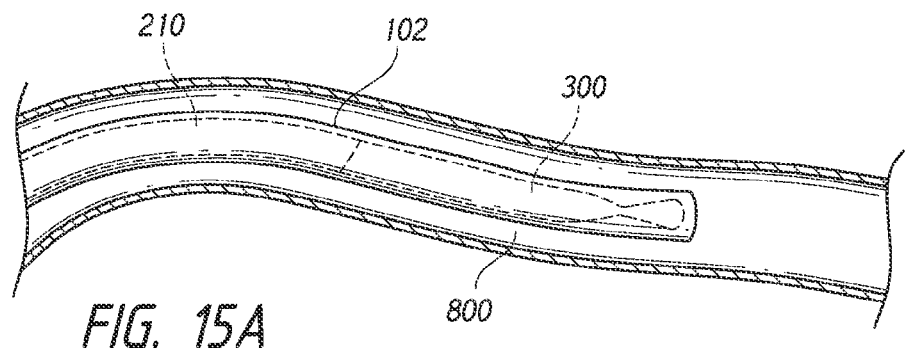
FIG. 15A-15D are sequential views of the expansion process of an implant, according to some embodiments.
Figure 15B:
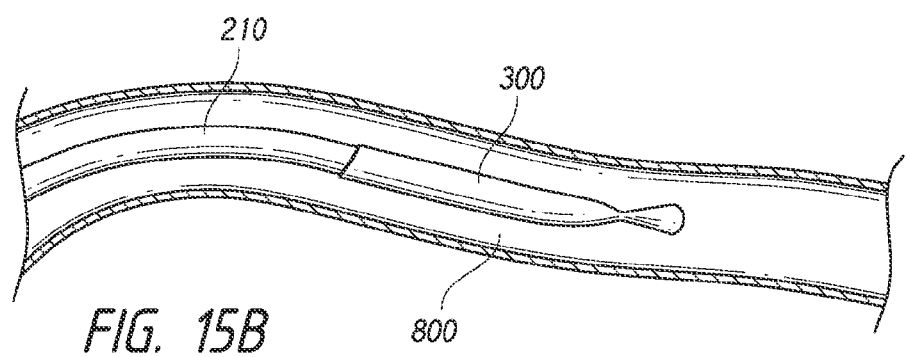
Figure 15C:
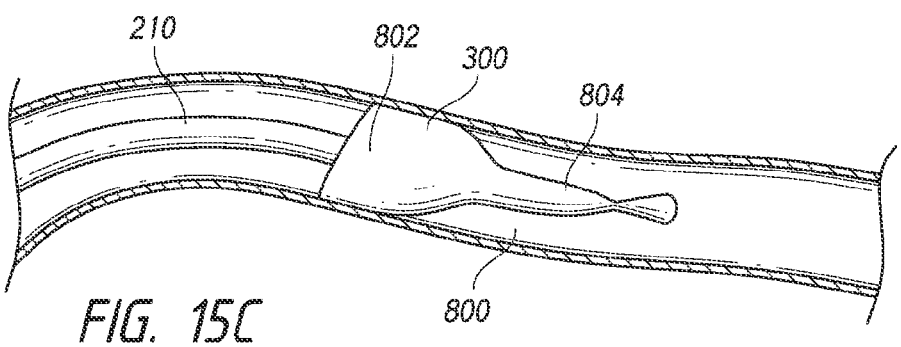
Figure 15D:
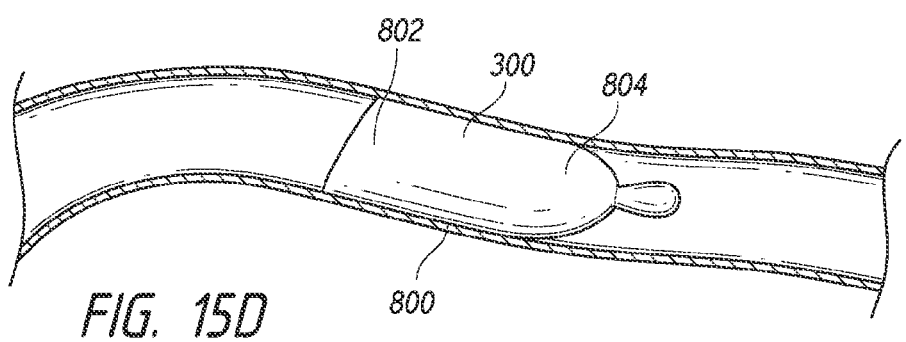

Referring now to FIG. 12-14, the implant carrier assembly 200 can also comprise the handle assembly 250. The handle assembly 250 can be used to deploy the proximal and distal sections 310, 312 of the implant 300. In some embodiments, the assembly 250 can include a deployment handle or body 710 with a side port 712 to accommodate syringe attachment to flush the catheter 210 of air and to pre-expand the cover member or cover member before deploying the implant.

The handle assembly 250 can also comprise at least one slider member configured to actuate an elongate member of the assembly 200. In the embodiment illustrated in FIG. 12, the handle assembly 250 can also be configured to comprise more than one slider member. As illustrated, the handle assembly 250 comprises first and second slider members 720, 722. The first and second slider members 720, 722 can be coupled to respective elongate members, such as elongate members 522, 520 of the embodiment illustrated in FIG. 7B.

Additionally, in accordance with some embodiments, the handle assembly 250 can also comprise one or more retention clips 730, 732. The retention clips 730, 732 can be configured to prevent movement of the slider members 720, 722 relative to the handle 710, thereby restricting movement of the elongate members 520, 522 and premature deployment of the implant. When the retention clips 730, 732 are removed, which may be done separately or together, the slider members 720, 722 can be used to release the proximal and distal ends of the implant. For example, the proximal slider member 720 can be configured to release the proximal end of the implant. Further, the distal slider member 722 can be configured to release the distal end of the implant. FIGS. 13-14 show stepwise movement of the slider members 720, 722 as the retention clips 730, 732 are removed from the handle 710 to permit proximal refraction of the slider members 720, 722. As shown, the clips 730, 732 can be removed from engagement with the handle 710, such as in slots 740, 742, thereby allowing the respective slider member 720, 722 to be unrestrained in a proximal direction.

Implant deployment can be performed as a two stage process, which is illustrated in FIGS. 15A-15D. The guide catheter 102 and implant can first be moved to a target location 800 (shown FIG. 15A). The guide catheter 102 can then be removed (shown in FIG. 15B). After the proximal-most retention clip is removed from the handle assembly, the proximal slider member of the handle assembly can be pulled proximally to release a proximal end 802 of the implant 300 (shown in FIG. 15C). The physician can flush the implant with fluid using a port in the handle to facilitate opening and release of the proximal end 802. When the proximal implant end 802 is released, the physician can check the implant position and observe as the inner space of the implant 300 fills with blood. Some slight movement of the implant 300 may be helpful to achieve precise placement. The second retention clip of the handle assembly can then be removed and the distal slider member of the handle assembly can be pulled proximally to release a distal end 804 of the implant (shown in FIG. 15D), thus releasing the entire implant 300.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying claims and their equivalents are intended to cover such forms or modifications as would fall within the scope and spirit of the inventions.

What is claimed is:

1. A method for manufacturing an occlusive device, the method comprising:
    positioning a first end section of a cover member over an aperture in an engagement section of a catheter;
    positioning a support member over the engagement section, thereby covering the first end section;
    inserting an end portion of the support member into the aperture;
    everting a second end section of the cover member over the first end section; and
    closing an end of the second end section.

2. The method of claim 1, wherein the support member is self-expanding, and the positioning the support member comprises compressing the support member onto the engagement section.

3. The method of claim 1, wherein the inserting comprises engaging an elongate member with the support member end portion in the aperture.

4. The method of claim 3, further comprising piercing the cover member to engage the elongate member with the support member end portion in the aperture.

5. The method of claim 3, wherein the engaging comprises positioning the elongate member within the aperture, radially between of the support member end portion and a wall of the catheter.

6. The method of claim 1, wherein the aperture is a first aperture and the support member end portion is a support member first end portion, and the method further comprises inserting a second end portion of the support member into a second aperture of the catheter, the second aperture being distal to the first aperture.

7. The method of claim 6, wherein the elongate member is a first elongate member, and the inserting the support member second end portion comprises engaging a second elongate member with the support member second end portion in the second aperture.

8. The method of claim 6, wherein the inserting the second end portion comprises engaging the elongate member with the support member second end portion in the second aperture.

9. The method of claim 1, wherein the closing the end of the second end section comprises suturing, clipping, or gluing the end.

10. The method of claim 1, wherein the positioning the first end section comprises positioning an end of the first end section longitudinally between the aperture and a distal end of the catheter.

11. The method of claim 1, wherein the positioning the first end section comprises positioning an end of the first end section longitudinally distal to a distal end of the catheter.

12. The method of claim 11, wherein the closing comprises coupling the first end section to the second end section.

13. The method of claim 11, wherein the first section comprises a plurality of strips.

* * * * *